(12) United States Patent (10) Patent No.: US 7,285,289 B2
Nagy et al. (45) Date of Patent: Oct. 23, 2007

(54) NANOPARTICLE VACCINES

(76) Inventors: Jon O. Nagy, 347 Little Wolfe Rd., Bozeman, MT (US) 59715; Robert F. Bargatze, 1302 Wildflower Way, Bozeman, MT (US) 59715; John W. Jutila, 516 S. Grand Ave., Bozeman, MT (US) 59715; Jim E. Cutler, 347 Millaudon St., New Orleans, LA (US) 70118; Pati M. Glee, 813 W. Villard #75, Bozeman, MT (US) 59715

( * ) Notice: Subject to any disclaimer, the term of this patent is extended or adjusted under 35 U.S.C. 154(b) by 0 days.

(21) Appl. No.: 10/413,607

(22) Filed: Apr. 14, 2003

(65) Prior Publication Data

US 2004/0022840 A1 Feb. 5, 2004

Related U.S. Application Data

(60) Provisional application No. 60/372,631, filed on Apr. 12, 2002.

(51) Int. Cl.
A61K 39/00 (2006.01)
A61K 9/127 (2006.01)
A61K 39/38 (2006.01)
A61K 9/14 (2006.01)
A61K 39/145 (2006.01)
A61K 49/00 (2006.01)
A61B 5/055 (2006.01)

(52) U.S. Cl. ............... 424/450; 424/9.321; 424/9.322; 424/9.34; 424/9.51; 424/1.21; 424/400; 424/490; 424/417; 424/184.1; 424/234.1; 424/204.1; 424/278.1; 424/206.1; 424/225.1; 424/272.1; 424/254.1; 424/229.1; 424/246.1; 424/227.1; 424/253.1

(58) Field of Classification Search ................ 424/450, 424/400, 812, 490, 184.1, 458, 185.1, 486, 424/9.321, 489, 9.322, 1.21, 9.51, 417, 246.1, 424/9.34, 260.1, 204.1, 225.1, 227.1, 229.1, 424/258.1, 256.1, 274.1, 248.1, 231.1; 514/2, 514/12
See application file for complete search history.

(56) References Cited

U.S. PATENT DOCUMENTS

| | | | | |
|---|---|---|---|---|
| 5,512,294 A | * | 4/1996 | Li et al. | 424/450 |
| 5,580,563 A | | 12/1996 | Tam | |
| 5,686,113 A | | 11/1997 | Speaker et al. | |
| 5,709,879 A | | 1/1998 | Barchfeld et al. | |
| 5,762,904 A | * | 6/1998 | Okada et al. | 424/1.21 |
| 5,962,422 A | | 10/1999 | Nagy et al. | |
| 5,985,852 A | | 11/1999 | Nagy et al. | |
| 6,001,395 A | * | 12/1999 | Coombes et al. | 424/501 |
| 6,004,534 A | * | 12/1999 | Langer et al. | 424/9.321 |
| 6,060,064 A | | 5/2000 | Adams et al. | |
| 6,060,082 A | | 5/2000 | Chen et al. | |
| 6,086,881 A | | 7/2000 | Frey et al. | |
| 6,090,406 A | | 7/2000 | Popescu et al. | |
| 6,132,764 A | * | 10/2000 | Li et al. | 424/450 |
| 6,225,445 B1 | | 5/2001 | Shen et al. | |
| 6,235,309 B1 | * | 5/2001 | Nagy et al. | 424/450 |
| 6,299,897 B1 | | 10/2001 | Nagy et al. | |
| 6,326,021 B1 | | 12/2001 | Schwendeman et al. | |
| 6,342,226 B1 | | 1/2002 | Betbeder et al. | |
| 6,350,466 B1 | * | 2/2002 | Li et al. | 424/450 |
| 6,387,397 B1 | * | 5/2002 | Chen et al. | 424/450 |
| 6,500,453 B2 | * | 12/2002 | Brey et al. | 424/450 |
| 6,511,677 B1 | * | 1/2003 | Brey et al. | 424/450 |
| 6,569,451 B1 | * | 5/2003 | Li et al. | 424/450 |
| 6,663,886 B2 | * | 12/2003 | Nagy et al. | 424/450 |
| 2002/0041861 A1 | * | 4/2002 | Brey et al. | 424/78.18 |
| 2003/0082103 A1 | * | 5/2003 | Wartchow et al. | 424/1.53 |
| 2003/0223938 A1 | * | 12/2003 | Nagy et al. | 424/46 |
| 2004/0022840 A1 | * | 2/2004 | Nagy et al. | 424/450 |
| 2004/0253184 A1 | * | 12/2004 | Li et al. | 424/9.363 |

FOREIGN PATENT DOCUMENTS

| | | | |
|---|---|---|---|
| WO | WO95/03035 A1 | * | 2/1995 |
| WO | WO99/33940 A1 | * | 7/1999 |
| WO | WO99/65465 A1 | * | 12/1999 |
| WO | WO 00/23955 | | 4/2000 |
| WO | WO 02/100325 | | 12/2002 |

OTHER PUBLICATIONS

Charych et al, Chemistry and Biology, 1996, 3:113120.*
Chen et al, Book of Abstracts, ACS National Mtg. Sep. 7-11, 1997 Abstract only.*
Keddy et al, Abstracts of Papers, ACS National Mtg, Aug. 26-30, 2001. Abstract only.*

(Continued)

*Primary Examiner*—Nita Minnifield
(74) *Attorney, Agent, or Firm*—Nixon Peabody LLP

(57) ABSTRACT

The present invention relates to nanoparticle vaccines comprised of a carrier, particularly polymerized lipids, having multiple copies of an antigen or combinations of different antigens displayed on the carrier. Such antigen-displaying nanoparticles may also display a targeting molecule on its surface in order to direct it to a specific site or cell type to optimize a desired immune response. The present invention also relates to encapsulating an antigen or combinations of different antigens within such nanoparticles, with or without a targeting molecule displayed on its surface. The antigens used in this invention are effective to produce an immune response against a variety of pathological conditions.

12 Claims, 10 Drawing Sheets

OTHER PUBLICATIONS

Pan et al, langmuir, 1997, 13:1365-1367.*
Walker, Vaccine, 1994, 12/5:387-400.*
Bowersock et al, Advanced Drug Delivery Reviews, 1999, 38:167-194.*
Kocisko et al, J. General Viorlogy, 2004, 85:2479-2483.*
Spevak et al, J. Med. Chem., 1996, 39:1018-1020.*
Alonso-Romanowski et al, Chemistry and Physics of Lipids, 2003, 122:191-203.*
Foster et al, Advanced Drug DeliveryReviews, 2003, 57:431-450.*
Barr et al, Advanced Drug Delivery Reviews, 1998, 32:247-271.*
Keegan et al, Biomaterials, 2003, 24:4435-4443.*
Singh et al, International J. Parasitology, 2003, 33:469-478.*
O'Hagan et al, Biomolecular Engineering, 2001, 18:69-85.*
Clark et al, Advanced Drug Delivery Reviews, 2001, 50:81-106.*
Brayden et al, Microbes and Infection, 2001, 3:867-876.*
Nishioka et al, Advanced Drug Delivery Reviews, 2001, 47:55-64.*
Chen, J. Controlled Release, 2000, 67:117-128.*
Engers et al, Parasitology Today, 1998, 14/2:56-64.*
Medina et al, Vaccine, 2001, 19:1573-1580.*
Jeong et al, J. Biotechonology, 2002, 94:255-263.*
Clark et al, Vaccine, 2002, 20:208-217.*
Honda et al, J. Mol. Biol., 1999, 287:293-300.*
Chen et al, J. Controlled Release, 1996, 42:263-272.*
Hayward et al, FEBS, 1985, 187/2:261-266.*
Okada et al, Pharmaceutical Research, 1995, 12/4:576-582.*
Fabani et al, J. Liposome Research, 2002, 12/1-2:13-27.*
Cohen, J. Liposome Research, 1995, 5/4:813-827.*
Ohno et al, Macromolecules, 1987, 20:929-933.*
Alison et al, FASEB J., Dec. 2003, 17/15:2296-2298.*
Chen et al, Pharmaceutical Research, 1996, 13/9:1378-1383.*
Torchilin et al, Polymer Science, 1988, 30/10:2307-2312.*
Patel et al, BBRC, 2001, 281:536-543.*
Chen et al, Polymeric Materials Science and Engineering, 1997, 77:599-600.*
Chen et al, Proceed. Intern. Symp. Control. Rel. Bioact. Mater., 1995, 22:204-205.*
Sivakumar et al, Reactive and Functional Polymers, 2001, 49/3:179-187.*
Freeman et al, Biochemical Society Transactions, 1987, 15/3:413-414.*
Gupta et al, Vaccine, 1996, 14/3:219-255.*
Ivins et al, European J. Epidemiology, 1988, 4:12-19.*
Welkos et al, Microbial Pathogenesis, 1988, 5/2:127-139 Abstract only.*
Patel et al, BBA, 1984, 797/1:20-26 Abstract only.*
Terzano et al, European J. Pharmaceutics and Biopharmaceutics, 2005, 59/1:57-62 Abstract only.*
Spevak et al, J. Am. Chem., 1993, 115:1146-1147.*
Vandegriff et al, Art. Cells Blood Subs. and Immob. Biotech., 1994, 22/3:849-854.*
Magalhaes et al, Biotechnol. Appl. Biochem., 2001, 33:61-64.*
Kesisoglou et al, Expert Opin. Drug Deliv., 2005, 2/3:451-463.*
El Baraka et a,, BBA, 1996, 1280:107-114.*
Discher et al, Science, 2002, 297:967-973.*
Kersten et al, Expert Rev. Vaccines, 2004, 3/4:453-462.*
Vastag, JAMA, 2002, 287/12:1516-1517.*
Zauner et al, Biol. Chem., 2001, 382:581-596.*
Flick-Smith et al, Infection and Immunity, 2002, 70/4:2022-2028.*
Bramwell et al, advanced Drug Delivery Reviews, 2005, 57:1247-1265.*
Reuveny et al, Infection and Immunity, 2001, 69/5:2888-2893.*
Moriya et al, Vaccine, 2002, 20:789-796.*
Wilson et al, Advanced Drug Delivery Reviews, 2005, 57:1392-1402.*
Welkos et al, Microbial Pathogenesis, 1988, 5:127-139.*
Ivins et al, Infection and Immunity, Feb. 1990, 58/2:303-308.*
Iacono-Connors et al, Infection and Immunity, Jun. 1991, 59/6:1961-1965.*
Girard et al, Vaccine, 2006, 24:4062-4081.*
Finco et al, Vaccine, 2005, 23:1178-1188.*
Ballou et al, Am. J. Trop. Med., 2004, 71/Suppl. 2:239-247.*
Clark et al., "Targeting Polymerised Liposome Vaccine Carriers to Intestinal M Cells," *Vaccine* 20:208-217 (2002).
Brayden et al., "Microparticle Vaccine Approaches to Stimulate Mucosal Immunisation," *Microbes and Infection* 3:867-876 (2001).
Jeong et al., "Enhanced Adjuvantic Property of Polymerized Liposome as Compared to a Phospholipid Liposome," *Journal of Biotechnology* 94:255-263 (2002).
J. Kreuter, "Nanoparticles and Microparticles for Drug and Vaccine Delivery," *J. Anat.* 189:503-505 (1996).
Lian et al., "Trends and Developments in Liposome Drug Delivery Systems," *Journal of Pharmaceutical Sciences*, 90(6):667-680 (2001).
B. Vastag, "Despite Finding Anthrax Vaccine Useful, IOM Recommends Seeking a Better One," *JAMA* 287(12):1516-17 (2002).
Brennan et al., "Cowpea Mosaic Virus as a Vaccine Carrier of Heterologous Antigens," *Molecular Biotechnology* 17:15-26 (2001).
Guan et al., "Liposomal Formulations of Synthetic MUC1 Peptides: Effects of Encapsulation Versus Surface Display of Peptides on Immune Response," *Bioconjugate Chem.* 9:451-458 (1998).
Rajananthanan et al., "Evaluation of Novel Aggregate Structures as Adjuvants: Composition, Toxicity Studies and Humoral Responses," *Vaccine* 17:715-730 (1999).
Zeng et al., "Highly Immunogenic and Totally Synthetic Lipopeptides as Self-Adjuvanting Immunocontraceptive Vaccines," *The Journal of Immunology* 169:4905-4912 (2002).
Říhová, "Immunomodulating Activities of Soluble Synthetic Polymer-Bound Drugs," *Advanced Drug Delivery Reviews* 54:653-674 (2002).
Sadler et al., "Synthetic Peptide Epitope-Based Polymers: Controlling Size and Determining the Efficiency of Epitope Incorporation," *J. Peptide Res.* 60:150-158 (2002).
Huang et al., "Lipophilic Multiple Antigen Peptide System for Peptide Immunogen and Synthetic Vaccine," *Molecular Immunology* 31(15):1191-1199 (1994).
Zeng et al., "Totally Synthetic Lipid-Containing Polyoxime Peptide Constructs are Potent Immunogens," *Vaccine* 18:1031-1039 (2000).
Chikh et al., "Attaching Histidine-Tagged Peptides and Proteins to Lipid-Based Carriers Through Use of Metal-Ion-Chelating Lipids," *Biochimica et Biophysica Acta* 1567:204-212 (2002).
Alonso-Romanowski et al., "Characterization of Diacetylenic Liposomes as Carriers for Oral Vaccines," *Chemistry and Physics of Lipids* 122:191-203 (2003).
Jeong et al., "Enhanced Adjuvantic Property of Polymerized Liposome as Compared to a Phospholipid Liposome," Journal of Biotechnology 94:255-263 (2002).

* cited by examiner

Figure 1. Examples of Conjugation Methods for Attachment of Antigen(s) or Ligands to Lipids.

Amide bond formation

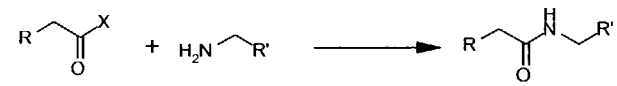

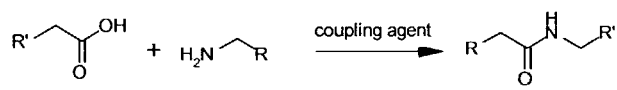

R = lipid  X = N-hydroxysuccinimide, pentafluorophenol, etc.  R' = protein, peptide, small molecule

Thioether or disulfide bond formation

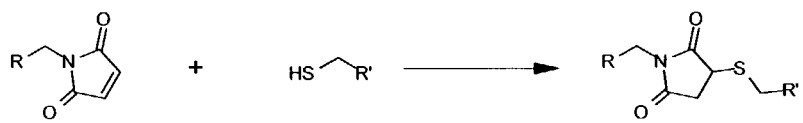

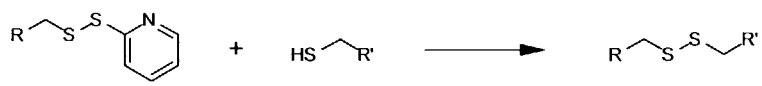

R = lipid  R' = protein, peptide, small molecule

Alkylation

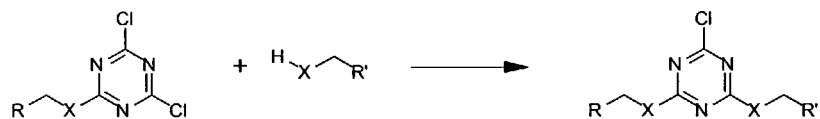

R = lipid  X = O, N, S  R' = protein, peptide, small molecule

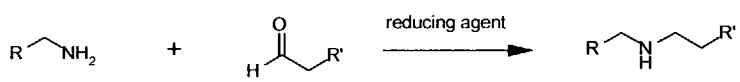

R = lipid  R' = glycoprotein, carbohydrate or polysaccharide, small molecule in the glycoprotein or polysaccharide the aldehyde functionality is generated as shown below

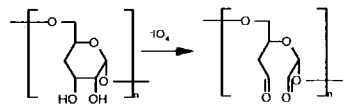

Chelation

Figure 2. Schematic of Nanoparticle Formed from Assembly of Antigen- or Targeting-Lipid and Charged or Uncharged Matrix Lipids.
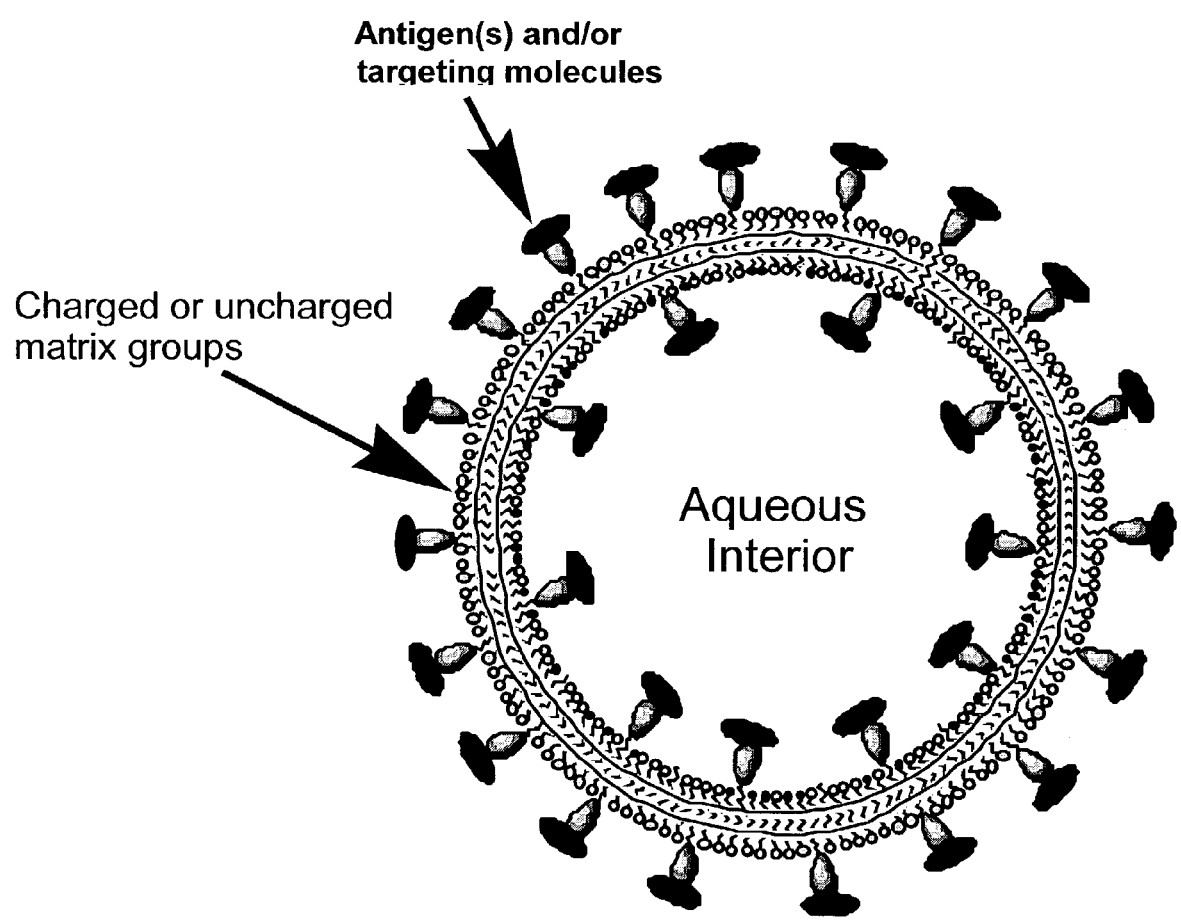

Figure 3. Depiction of Attaching Surface-Displayed Molecules to a Pre-Formed Nanoparticle.
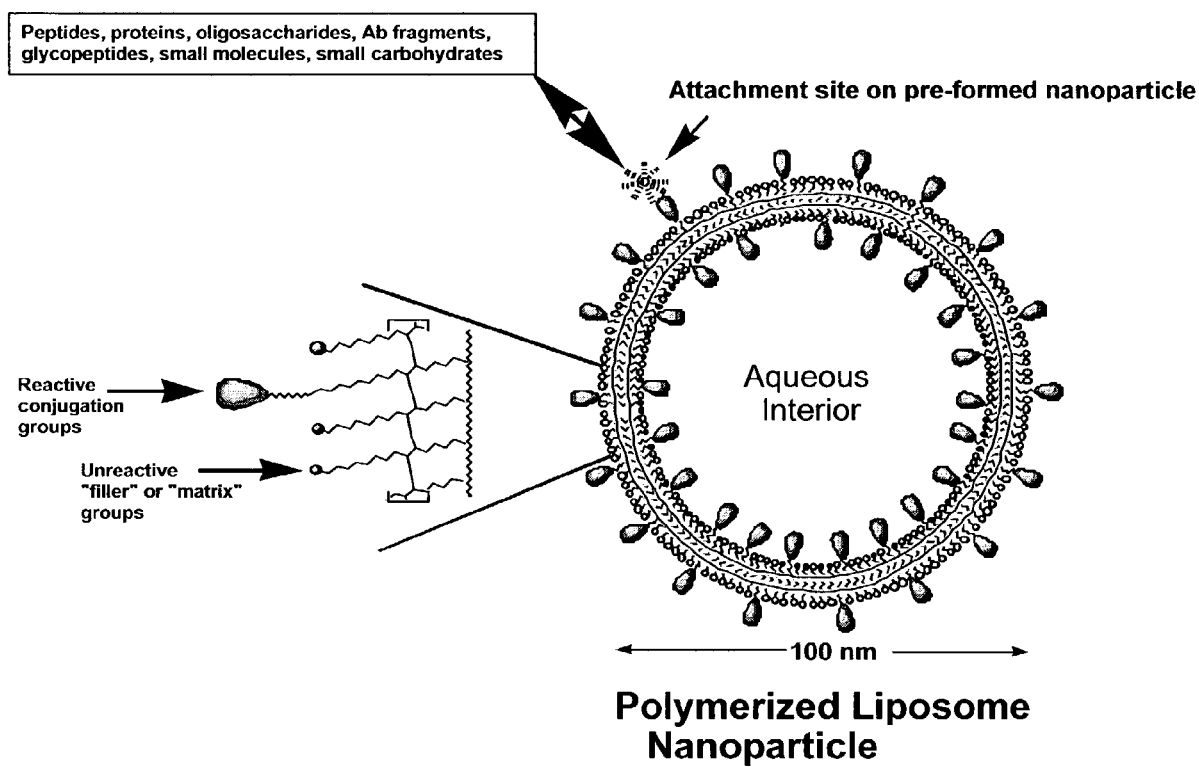

Figure 4. Schematic of Nanoparticle Encapsulating Antigen, in this Case Showing Targeting Molecules on the Nanoparticle Surface.

Figure 5. Protective Efficacy of *Candida* Glycoprotein-Nanoparticles
(glycoproteins conjugated to lipid monomers followed by nanoparticle polymerization)
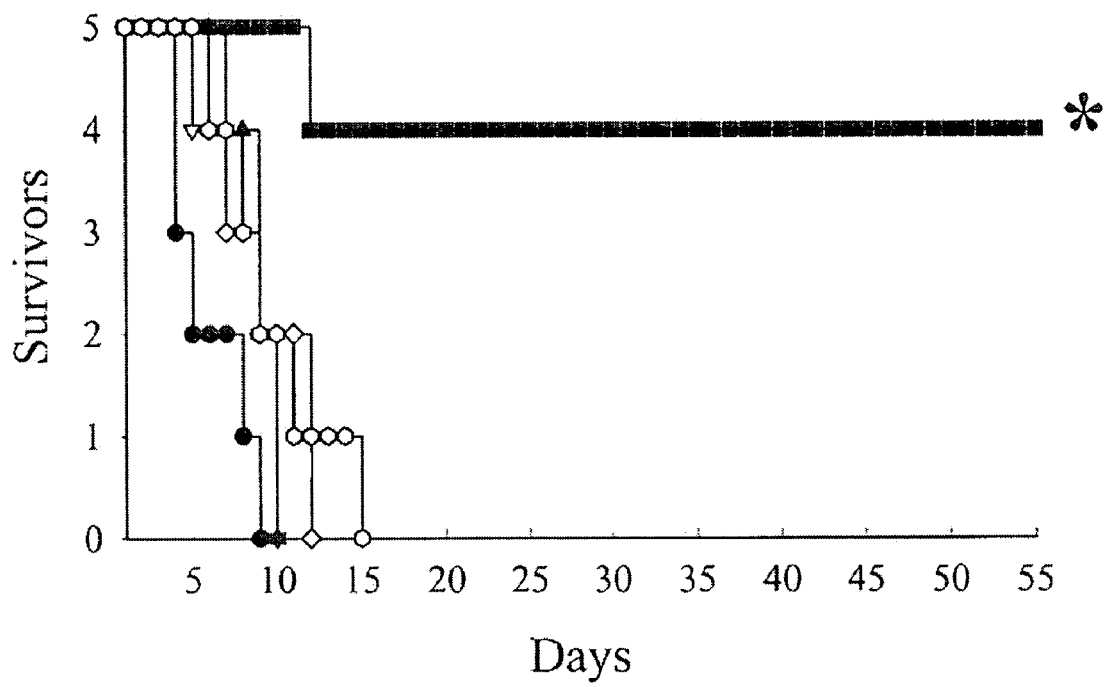
| | MST (days) |
|---|---|
| —●— Diluent (DPBS) | 6.0 ± 2.3 |
| —▽— Adjuvant (Adj.) only | 8.4 ± 2.1 |
| —■— JN#100-1/Adj. | 47.2 ± 19.2 |
| —◇— JN#100-2/Adj. | 9.2 ± 2.8 |
| —▲— JN#100-3/Adj. | 9.0 ± 1.2 |
| —○— JN#100-4/Adj. | 9.8 ± 3.4 |
\* Kidney cfu's of the 4 survivors:
18, 52, 62, and 79 x $(10^3)$ total cells, respectively Figure 6. Protective Efficacy of *Candida* Glycoprotein-Nanoparticles (glycoproteins conjugated to pre-formed nanoparticles).
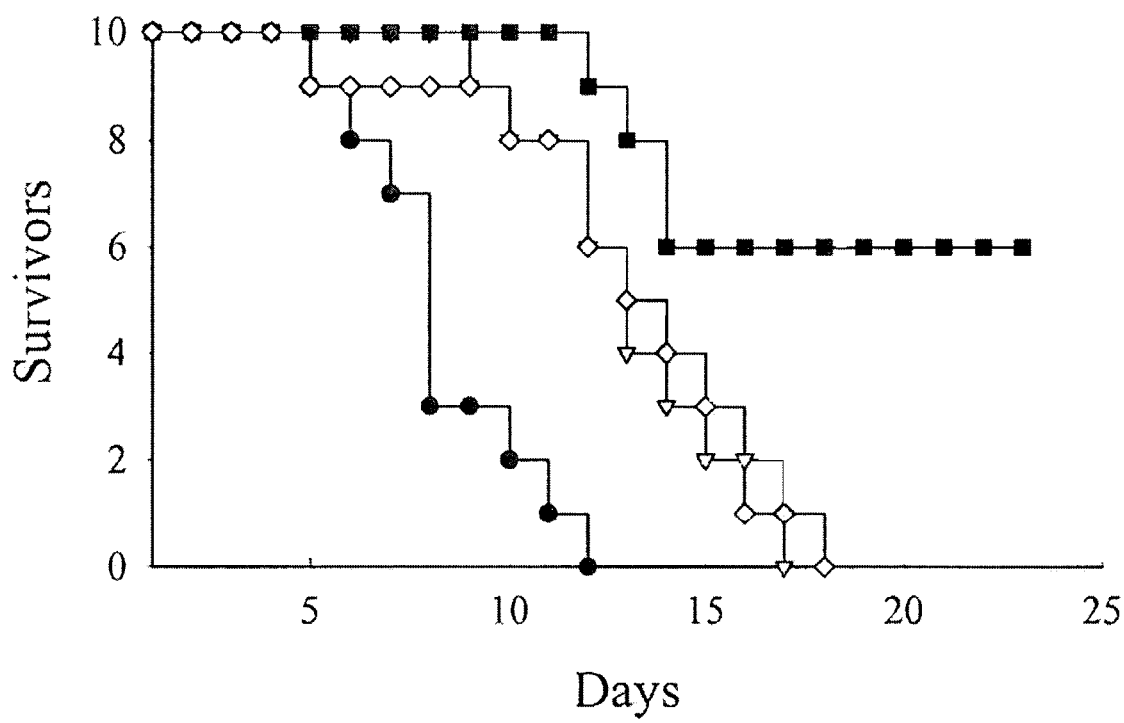

Figure 7. ELISA Screens of Total Igs (G + M + A) in Serum from Immunized Mice.
Panel A
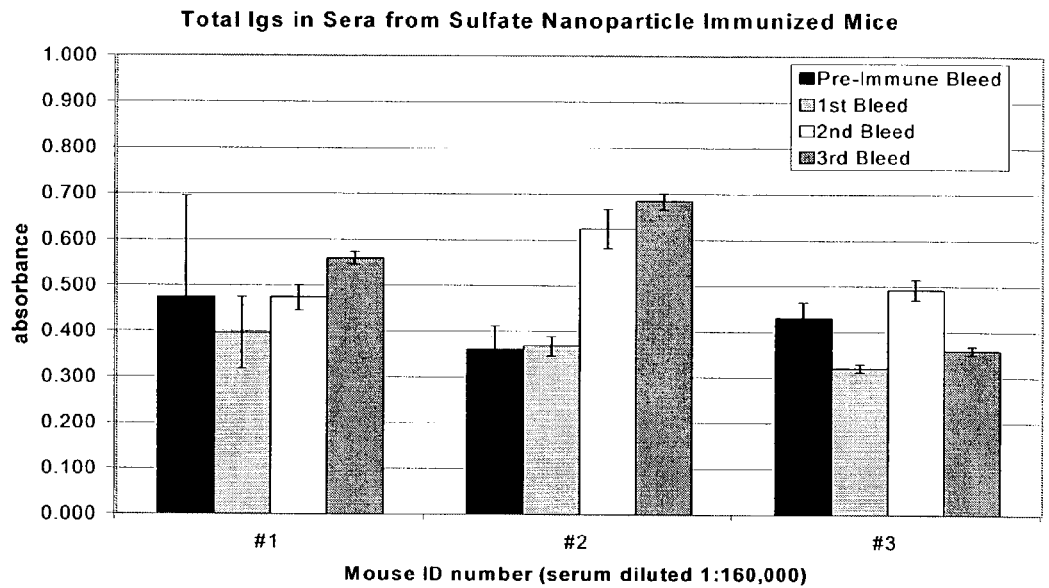
Panel B
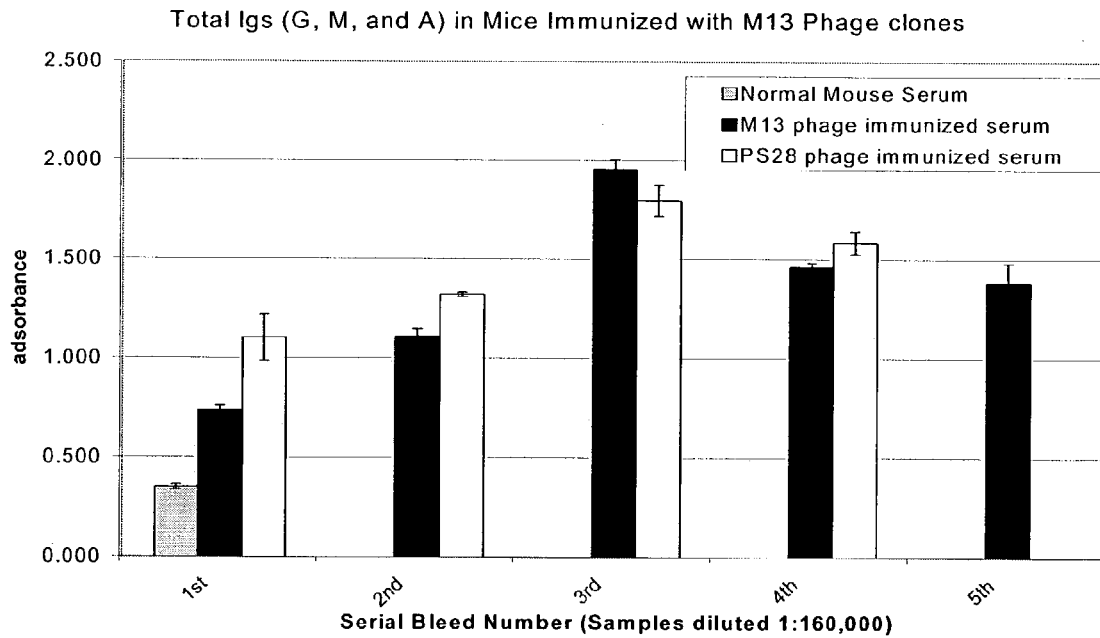

Figure 8. ELISA Screening for Nanoparticle-Specific Antibody Responses.
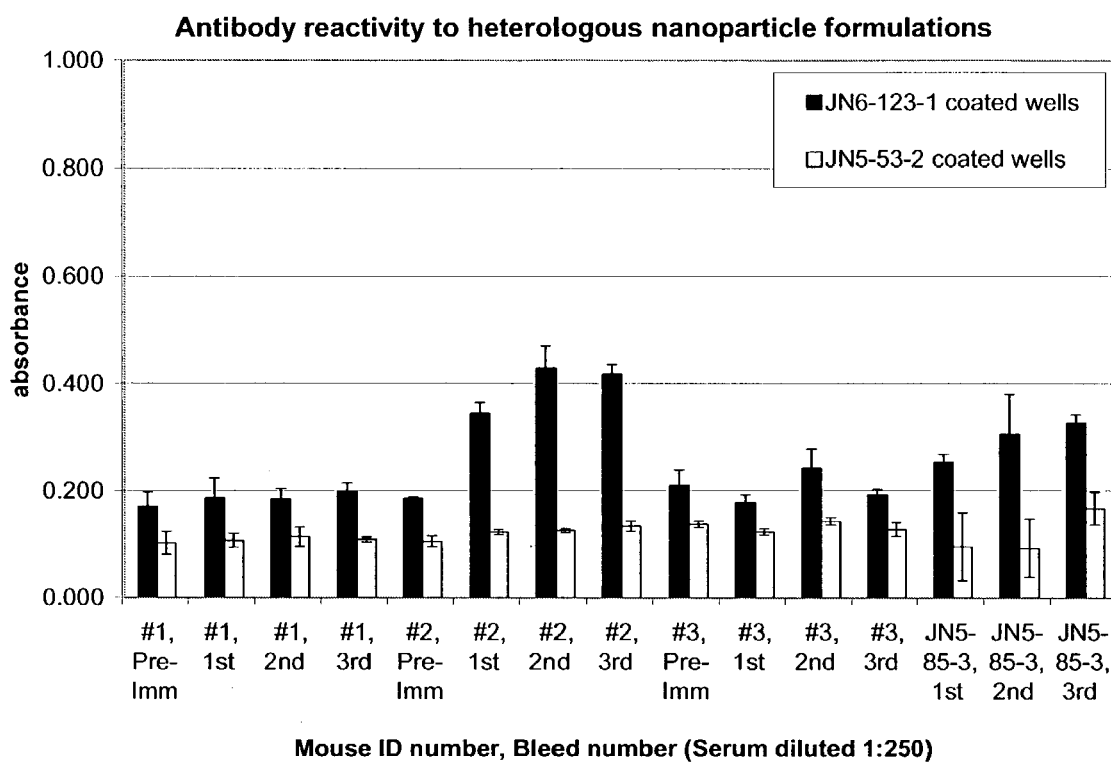

Figure 9. PZP – Nanoparticle Rabbit Contraceptive Vaccine Study.
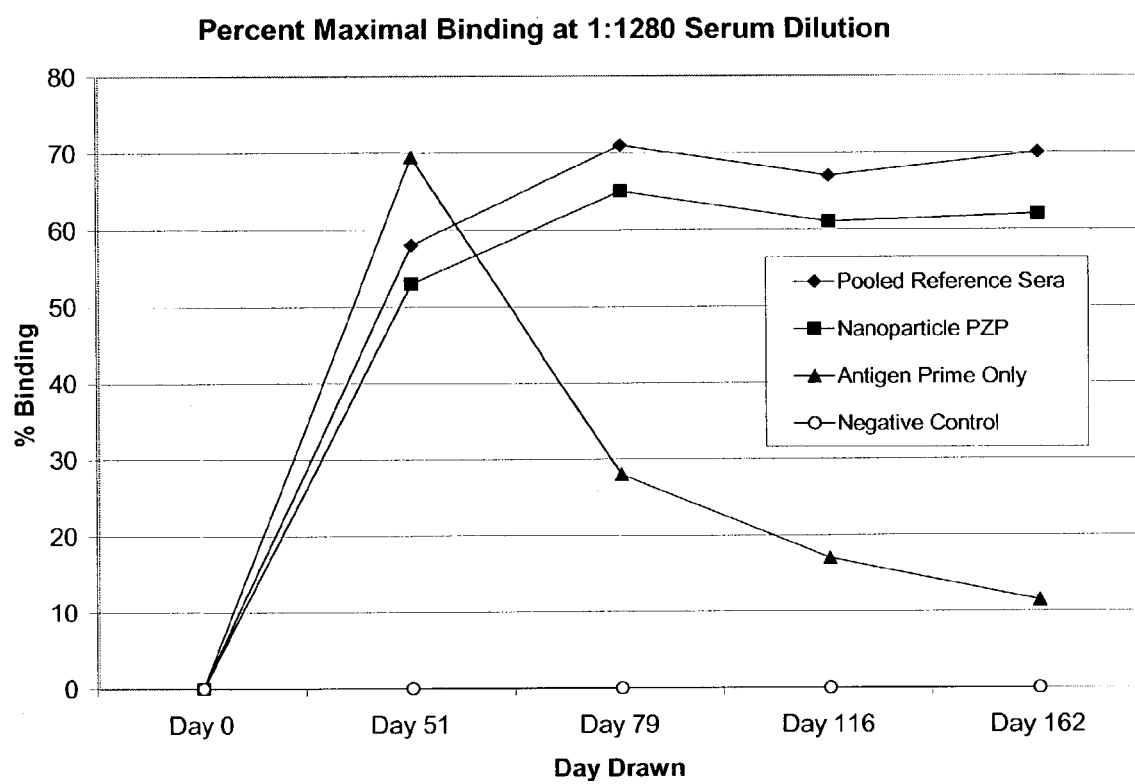

Figure 10. PZP – Nanoparticle Wild Horse Contraceptive Vaccine Study.
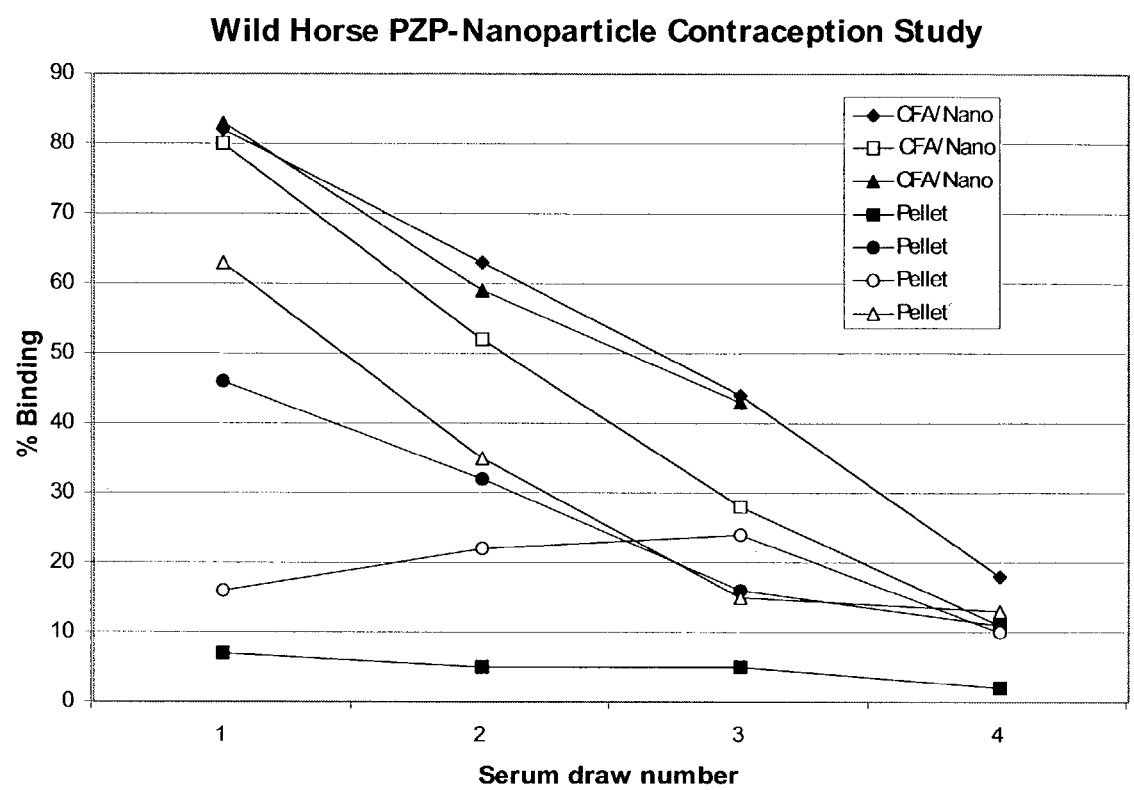

NANOPARTICLE VACCINES

This application claims the benefit of U.S. Provisional Patent Application Ser. No. 60/372,631, filed Apr. 12, 2002.

ACKNOWLEDGMENT OF FEDERAL SUPPORT

The disclosed invention was made in part during work partially supported by the National Institute of Health under contract PO1 AI37194. The United States government has certain rights in the invention.

FIELD OF THE INVENTION

The present invention relates to nanoparticle vaccines, comprised of polymerized liposomes, that carry multiple copies of an antigen or combinations of different antigens or carry antigens inside of targeted liposomes and are capable of producing a protective immune response.

BACKGROUND OF THE INVENTION

Infectious diseases have plagued human populations throughout history and still cause the death of millions each year. Both human and other vertebrate organisms become infected with a broad array of microbial pathogens including bacteria, viruses, fungi, and protozoa. Products, which we have developed to protect against infectious diseases, consist primarily of antibiotics and vaccines. However, conventional antibiotics continue to become less effective due to the increased resistance of infectious organisms.

The prevention of clinical symptoms and pathogenic processes via the use of vaccines is considered one of the most effective and desired procedures to combat illness. In this art, antigens or immunogens are introduced in a manner that stimulates an immune response in the host organism prior to infection in order to protect against the infectious disease. However, for many infectious diseases, including malaria, tuberculosis, anthrax, tularemia, brucellosis, Hepatitis C infections, histoplasmosis, coccidioidomycosis, viral hemorrhagic fevers, bubonic plaque, viral encephalitis, Yellow Fever, and viral and bacterial gastroenteritis, there remains no available or effective vaccine.

Multivalent Carriers and Liposome Nanoparticles

In any composition suitable for use as a vaccine, it is essential that the conformational integrity and immunogenic epitopes and antigenic sites be preserved intact. Changes in the structural configuration, chemical charge, or spatial orientation of these molecules and compounds may result in partial or total loss of antigenic activity and utility. The ability of an associated carrier particle to have minimal undesirable reactions in the vaccine and yet facilitate interaction of the antigenic compound with the immune system are primary concerns. All of these factors must be taken into account when preparing a composition as a conjugate that is to be used as a vaccine or as biomaterial for recognition of specific receptors.

It is also well known that many biological systems interact through multiple simultaneous molecular contacts. See, e.g., a comprehensive review by Mammen, et al., "Polyvalent Interactions in Biological Systems: Implications for Design and Use of Multivalent Ligands and Inhibitors," *Angew. Chem. Int. Ed.* 37:2754-2794 (1998). These authors describe a wide variety of polyvalent reagents and the binding interactions between such reagents and various targets, but not in the context of vaccines.

Numerous multivalent constructs have been described in the literature. Brennan, et al., "Cowpea Mosaic Virus as a Vaccine Carrier of Heterologous Antigens," *Mol. Biotechnol.* 17(1):15-26 (2001), discusses chimeric virus particles as carriers of heterologous antigens. In particular, the viral capsid shell was used as a presentation system for antigenic epitopes derived from a number of vaccine targets and inmunizations and resulted in humoral and cellular immune responses against the antigens. U.S. Pat. No. 6,060,064 to Adams, et al., also describes use of a protein carrier used to display immunogenic amino acid sequences for use as a vaccine. Although protein carriers can be effective, it is widely known that it is difficult to produce protein carriers using synthetic chemical methods, resulting in their use being time-consuming and expensive. Additionally, the coupling of an antigen to a protein carrier can alter the immunogenic determinants of the antigen. In many cases a robust immune response can be generated toward the protein carrier and a very minimal response to the hapten.

Other carrier types that have been used as multivalent vaccine constructs include metallic oxide particles (U.S. Pat. No. 6,086,881 to Frey, et al.); polysaccharide-based spermine, alginate capsules, which are non-synthetic (U.S. Pat. No. 5,686,113 to Speaker, et al.); and synthetic biocompatible base polymer of poly lactide-co-glycolide (U.S. Pat. No. 6,326,021 to Schwendeman, et al.). Each of these materials relies on a method of derivatizing a pre-formed particle and the loading of antigen is difficult to control.

Nanoparticle carriers for use as vaccine have also been made from lipids or other fatty acids (U.S. Pat. No. 5,709,879 to Barchfeld, et al.; U.S. Pat. No. 6,342,226 to Betbeder, et al.; U.S. Pat. No. 6,090,406 to Popescu, et al.; Lian, et al., Trends and Developments in Liposome Drug Delivery Systems, *J. of Pharma. Sci.* 90(6):667-680 (2001), and van Slooten, et al., Liposomes Containing Interferon-gamma as Adjuvant in Tumor Cell Vaccines, *Pharm Res.* 17(1):42-48 (2000)), as well as non-lipid compositions (Kreuter, "Nanoparticles and Microparticles for Drug and Vaccine Delivery," *J. Anat.* 189:503-505 (1996)). These described compositions are traditional bilayer or multilamellar liposomes, and are phospholipid based. Such liposomes are physically and chemically unstable, and rapidly leak encapsulated material and degrade the vesicle structure. Without stabilization of the liposome structure, they are not good candidates for oral drug or antigen delivery.

Phospholipids make up the bulk of cell membranes in the body. Phospholipid liposome based carriers have several disadvantages. Being natural-occurring substances, utilized in the membranes of a wide range of pathogenic organisms, the body has devised sensitive ways for differentiating between self and non-self membranes. Part of the protection of "self" comes from the decorations (such as carbohydrates) found on the extracellular side of the phospholipid membranes. Things entering with altered or different "decorations" are recognized as foreign and targeted for opsinization (clearance). Naked (undecorated) phospholipid membranes such as phosphotidylcholine (PC) liposome are rapidly cleared from circulation. This is accomplished by recognition by the RES cells and enzymatic degradation by the body's phospholipases. These enzymes rapidly metabolize phospholipid materials (Waite, *The Phospholipases* Plenum Press, NY (1987)). To retard this process, decoration of the PC membrane with "stealthing" agents, such as polyethylene glycol polymers has been applied. These large polymers shield the phospholipid surface from being "seen" by the immune system. If one uses a phospholipid based carrier, one must employ the cumbersome technique of either "stealthing" the surface or decorating it to resemble the body's own cell membranes in order to insure that the carrier circulates long enough to reach its target.

Another disadvantage of phospholipid liposome based carriers is that many of the lipid components are isolated from plant or animal tissues. This can raise concerns as to the levels of contaminants, such as endotoxins, that might be present in the preparations.

The third disadvantage is that the phospholipid liposome membranes are fluid, i.e. lipid components can move around changing their spatial orientation toward one another. Alteration in the spatial relationship between presented antigens can give rise to particles that have reduced immunogenicity (Chackerian, et al., "Induction of Autoantibodies to Mouse CCR5 with Recombinant Papillomavirus Particles," *Proc. Natl. Acad. Sci. USA* 96(5):2373-2378 (1999)).

A fourth disadvantage to phospholipid based liposomes arises from their propensity to fuse to cell membranes or other administered lipid carriers that can result in an amalgamation and loss of specific particles, particle contents or particle size uniformity, and therefore, lead to ineffectiveness of a vaccine or therapeutic based on such materials.

Polymerization of lipid-based nanoparticles creates a stable structure that does not readily fuse with other polymerized liposome nanoparticles or cell membranes, and therefore these nanoparticle vaccine carriers can maintain their small and uniform size. Polymerized liposome nanoparticles have been described in various patent and journal publications. For example, U.S. Pat. No. 6,004,534 to Langer, et al.; Brayden, et al., "Microparticle Vaccine Approaches to Stimulate Mucosal Immunisation," *Microbes and Infection* 3(10):867-876 (2001); Clark, et al., "Targeting Polymerized Liposome Vaccine Carriers to Intestinal M Cells," *Vaccine* 20:208-217 (2002); and Chen, et al., "Lectin-bearing Polymerized Liposomes as Potential Oral Vaccine Carriers," *Pharm. Res.* 13(9):1378-1383 (1996), relate to targeted polymerized liposomes for oral and/or mucosal delivery of encapsulated material as vaccines, allergens and therapeutics. Jeong, et al., "Enhanced Adjuvantic Property of Polymerized Liposome as Compared to a Phospholipid Liposome," *J. Biotech.* 94:255-263 (2002), also describes encapsulation of materials in a polymerized liposome, which is non-targeted. These references all describe encapsulation of materials in phospholipid-based polymerized nanoparticles. The disadvantages of phospholipid-based carriers have been discussed above.

SUMMARY OF THE INVENTION

The present invention is based, in part, on the discovery that nanoparticle vaccines having multivalent surface antigens (presented on the exterior or interior or the particle) or encapsulated antigens elicit significantly increased immune responses (Guan, et al., "Liposomal Formulations of Synthetic MUC1 Peptides: Effects of Encapsulation Versus Surface Display of Peptides on Immune Responses," *Bioconj. Chem.* 9:451458 (1998), which is hereby incorporated by reference in its entirety). Additionally, co-display of targeting molecule(s) on the polymerized liposome nanoparticle for purposes of directing the vaccine to a specific in vivo location increases the efficiency and effectiveness of the desired immune response.

Polymerization of the membrane greatly "freezes" the positions of the items displayed on the particle surface. As presentation of antigenic elements in a polyvalent array is believed to be an important contributor toward promoting an immunological response (Chackerian, et al., "Induction of Autoantibodies to Mouse CCR5 with Recombinant Papillomavirus Particles," *Proc. Natl. Acad. Sci. USA* 96(5): 2373-2378 (1999), which is hereby incorporated by reference in its entirety), a fixed surface-displayed rigid array is likely to be a more successful antigenic presenter than a fluid surface. Once the polymerized particle is prepared and assayed for vaccine effectiveness surface changes which may alter its activity or toxicity are unlikely to occur.

In the present invention, antigens may also be contained inside the nanoparticle, with or without surface displayed antigens and/or targeting molecules, depending upon the specific disease application. The present invention provides compositions and methods for use in various pharmaceutical applications, including vaccinating a subject for protection against infection by a pathogenic agent or for vaccination of a subject for resolution of a chronic infectious disease. Such subjects may include humans and wild or domestic animal populations such as bison, elk, cows, horses, sheep, goats, pigs, fowl, cats and dogs, although this invention may be applied to other species as well. Administration of the vaccine of this invention may be carried out orally, intradermally, intermuscularly, intraperitoneally, intravenously, subcutaneously, intranasally, sublingually, buccally, vaginally, or rectally.

In a preferred embodiment, the present invention relates to a nanoparticle that comprises a carrier, and polymerized liposome carriers are preferred, although various other carriers known to persons skilled in the art also would be appropriate. The polymerized liposome carrier may be either phospholipid or non-phospholipid based. The carrier preferably carries or displays (on the interior or exterior) multiple copies of antigen or combination of different antigens and targeting molecules. In another preferred embodiment the antigen-displaying carrier does not include targeting molecule(s). In a third preferred embodiment, the carrier displays antigen or a combination of different antigens and a targeting molecule on its surface, and encapsulates antigen or a combination of antigens within the nanoparticle. In another preferred embodiment, the antigen-displaying carrier encapsulates antigen(s) but does not display targeting molecule(s). In yet another preferred embodiment, the carrier displays targeting molecule(s) without antigen on its surface and encapsulates antigen or a combination of antigens within the nanoparticle.

According to the methods and compositions of the present invention, surface exposed antigen(s) and/or targeting molecule(s) may be attached to the nanoparticles by any means known in the art. Conjugation methods of this invention include chemical complexing, which may be either ionic or non-ionic in nature, or covalent binding. Such conjugation of antigen or targeting molecule may occur to reactive head groups of individual lipid monomers, or a collection of lipid monomers prior to assembly of the nanoparticle. Alternatively the antigen or targeting molecule can be attached to reactive head groups after the polymerized nanoparticle is formed.

The antigen or antigens of the present invention that are displayed on or within the nanoparticle induce an immune response against onset of disease caused by a variety of pathogenic conditions. In a preferred embodiment, the antigen may be derived from, but are not limited to, pathogenic bacterial, fungal, or viral organisms, *Streptococcus* species, *Candida* species, *Brucella* species, *Salmonella* species, *Shigella* species, *Pseudomonas* species, *Bordetella* species, *Clostridium* species, Norwalk virus, *Bacillus anthracis, Mycobacterium tuberculosis*, human immunodeficiency virus (UV), *Chlamydia* species, human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, bacterial disease agents, cancer cells, or mixtures thereof Other preferred embodiments include self-antigens for the treatment or prevention of autoimmune diseases. Another preferred embodiment includes adhesins or surface exposed cell signaling receptors or ligands. In still another preferred embodiment, the targeting agent or molecule directs the vaccine to a mucosal membrane. In yet another preferred embodiment, adjuvant(s) may be incorporated in the vaccine.

The nanoparticle vaccines of the present invention are superior to other platforms for several reasons: the spheroid assemblies are simple and inexpensive to synthesize and are very stable; the structures are polymerized to be "rigid", not suffering from folding uncertainties, unlike conventional bilayer liposomes, they are inert with regard to random fusion with themselves or cell membranes; and the surface character and displayed molecular orientation is easily manipulated because the polymer backbone tolerates nearly any appended molecule in a wide range of ratios. Therefore, it is an object of the present invention to provide new methods and compositions for a superior nanoparticle-based multivalent vaccine against a broad range of diseases and disorders.

BRIEF DESCRIPTION OF THE DRAWINGS

FIG. 1—Examples of Conjugation Methods for Attachment of Antigen(s) or Ligands to Lipids.

All of the commonly used methods for the conjugation of hapten, antigens, small molecules, carbohydrates and peptides are applicable to lipids. Lipids are readily made with various functional groups that permit conjugation to other molecules.

FIG. 2—Schematic of Nanoparticle Formed from Assembly of Antigen- or Targeting-Lipid and Charged or Uncharged Matrix Lipids.

Nanoparticles with presentation of antigen(s) and/or targeting molecules are prepared from preformed lipid-antigen/targeting molecule conjugates and charged or uncharged matrix lipids. This allows careful control of surface density and spacing of the ligands.

FIG. 3—Depiction of Attaching Surface-Displayed Molecules to a Pre-Formed Nanoparticle.

Nanoparticles can be prepared with various functional groups presented on the surface. These functional groups can then be conjugated to various ligands. If several different functional groups are present they can be selectively conjugated to different ligands. This allows the presentation of several different ligands on the surface of a single nanoparticle.

FIG. 4—Schematic of Nanoparticle Encapsulating Antigen, in this Case Showing Targeting Molecules on the Nanoparticle Surface.

Antigen can be encapsulated in a nanoparticle by forming the liposome in the presence of an aqueous solution of the antigen. Targeting molecules may be surface-displayed by methods described herein, or absent, depending on the desired characteristics of the nanoparticle.

FIG. 5—Protective Efficacy of *Candida* Glycoprotein-Nanoparticles (Glycoproteins Conjugated to Lipid Monomers Followed by Nanoparticle polymerization).

Mean survival time (MST) study of mice vaccinated with *Candida* glycoprotein Nanoparticles, where the *Candida* glycoproteins were conjugated to monomer lipids and then polymerized with matrix lipids into nanoparticles. BALB/c female mice were vaccinated twice (booster on day 21) with *Candida* cell wall glycoproteins in nanoparticle formulations containing different matrix lipids (JN#100-1 matrix lipid=Anionic COOH, JN#100-2 matrix lipid=neutral OH, JN#100-3 matrix lipid=Anionic $SO_3$, JN#100-4 matrix lipid=Cationic $NH_2$) in the presence of adjuvant (Complete Freund Adjuvant for first dose, Incomplete Freund Adjuvant for second dose) or vaccinated with adjuvant alone or Dulbecco's phosphate buffered saline (DPBS) diluent alone. On day 28, mice were challenged i.v. with live *C. albicans* yeast ($5\times10^5$ CFUs per mouse in 0.2 ml DPBS) and animals were monitored twice daily to assess survival. Vaccination with the JN#100-1 formulation demonstrated significantly greater MST values compared to any other treatment group. Survivors were assessed for *Candida* CFUs in the kidney (a target organ of disseminated disease) and numbers of live yeast remaining were comparable to earlier protection studies where vaccinations were with *Candida* glycoprotein liposomes or carrier protein conjugates.

FIG. 6—Protective Efficacy of *Candida* Glycoprotein-Nanoparticles (Glycoproteins Conjugated to Pre-Formed Nanoparticles).

Mean survival time (MST) study of mice vaccinated with *Candida* glycoprotein Nanoparticles, where the glycoproteins were conjugated to pre-formed nanoparticles. BALB/c female mice were vaccinated twice (booster on day 21) with *Candida* glycoprotein nanoparticle formulations containing different matrix lipids (JN#133-1 or JN#133-2) in the presence of adjuvant (Complete Freund Adjuvant for first dose, Incomplete Freund Adjuvant for second dose) or vaccinated with adjuvant alone or DPBS diluent alone. On day 28, mice were challenged i.v. with live *C. albicans* yeast ($5\times10^5$ CFUs per mouse in 0.2 ml DPBS) and animals were monitored twice daily to assess survival. Vaccination with the JN#133-1 formulation demonstrated significantly greater MST values compared to other treatment groups.

FIG. 7—ELISA Screens of Total Igs (G+M+A) in Serum from Immunized Mice.

Panel A: Serum antibody levels in sulfated nanoparticle immunized mice. BALB/c mice were bled for pre-immune serum samples and then were given 100 μl JN#6-123-1 nanoparticles without adjuvant i.p. on days 21, 35, and 49. The JN#6-123-1 nanoparticle batch was formulated by polymerizing matrix lipids at a ratio of 25% sulfate and 75% hydroxyl groups. Serum samples from the mice were obtained on day 28, 42, and 56 (the $1^{st}$, $2^{nd}$, and $3^{rd}$ bleeds, respectively). The graph shows serum samples at 1:160,000 dilution assessed for changes in total immunoglobulin levels by capture ELISA, as described in Example 4. Mice #1 and #2 show slight increases in antibody levels while total Igs levels for mouse #3 fluctuated and did not appear to correlate with the immunization regimen.

Panel B. Serum antibody levels in virally immunized mice. In parallel ELISAs, serum samples from mice immunized with M13 viral clones (M13KBst and PS28 phage) showed substantial increases in total Ig levels in response to booster immunizations, compared to serial samples in Panel A.

FIG. 8—ELISA Screening for Nanoparticle-Specific Antibody Responses.

Microtiter wells were coated with the sulfated nanoparticles JN#6-123-1 or an irrelevant nanoparticle and assayed for antibody binding in ELISA screens. The irrelevant controls for this assessment included a peptide-conjugated nanoparticle JN#5-53-2 (PS76 peptide—YRQFVTGFW (SEQ ID NO:1) in an 85% hydroxyl matrix lipid) and irrelevant serum samples from mice immunized with a similar PS76-nanoparticle JN#5-85-3, which failed to produce peptide specific responses in that formulation. Serum samples were diluted 1:250 and assessed for IgG+IgM+IgA antibodies binding to the nanoparticle coated wells, as described in Example 4. The data indicate that sulfated nanoparticle-coated wells bound more antibody from all serum samples, including serum from JN#5-85-3 immunized mice. The minimal if any booster effect noted for sulfated nanoparticle doses suggests a lack of specific immune responses. These observations support a non-specific mechanism of antibody binding that may be related to the anionic charge of the sulfated particles. These assays demonstrate the low immunogenicity of nanoparticle materials alone.

FIG. 9—PZP—Nanoparticle Rabbit Contraceptive Vaccine Study.

PZP was encapsulated in polymerized nanoparticles and tested as a contraceptive vaccine in rabbits. A mixture of EAPDA (256 mg) and sulfo-EAPDA (107 mg) were sonicated for 30 min. in 4 ml of an aqueous solution of PZP (2.6 mg/ml). The PZP-encapsulating liposomes were polymerized by exposure to UV light for approx. 5 min. The highly colored polymerized nanoparticles were then sterile filtered (0.2 u) and dialyzed to remove any non-encapsulated PZP. The material was then biologically evaluated.

Rabbits were inoculated intramuscularly. The data presented show nanoparticle vs. positive and negative treatments for immunization of rabbits as follows:

Rabbit S: nanoparticles injected twice (no adjuvant), two weeks apart.

Rabbit N (positive control): PZP+modified Complete Freund Adjuvant (mCFA) twice, two weeks apart.

Rabbit AT: PZP+mCFA and nanoparticles injected simultaneously, once only.

Rabbit E (Negative Control): mCFA injected twice, two weeks apart.

% Maximum binding (y axis) vs. serum draw dates (x axis) of rabbit sera (diluted 1:1280) for specific PZP antibody binding, referenced to PZP injected control animals (100%) as measured by ELISA.

The results presented in this figure show a high and sustained antibody response in rabbits injected only once, with PZP-nanoparticles in combination with adjuvant, that are comparable to that of the twice injected PZP positive control.

FIG. 10—PZP—Nanoparticle Wild Horse Contraceptive Vaccine Study.

PZP glycoprotein was encapsulated in nanoparticles and administered to horses as a contraceptive vaccine. A mixture of EAPDA (256 mg) and sulfo-EAPDA (107 mg) were sonicated for 30 min. in 4 ml of an aqueous solution of PZP (2.6 mg/ml). The PZP-encapsulating liposomes were polymerized by exposure to UV light for approx. 5 min. The highly colored polymerized nanoparticles were then sterile filtered (0.2 u) and dialyzed to remove any non-encapsulated PZP. The material was then biologically evaluated.

The horses were wild but in captivity. Seven mares were divided into two treatment groups for intramuscular injection as follows:

Three mares treated with 65 µg PZP emulsified in 0.5 ml Complete Freund Adjuvant (CFA)+100 µg PZP encapsulated in nanoparticles Four mares treated with 200 µg PZP incorporated in lactide-glycolide pellets.

% Maximum binding (y axis) vs. serum draw dates (x axis) of horse sera (diluted 1:1280) for specific PZP antibody binding, referenced to PZP injected control animals (100%) as measured by ELISA.

The data presented in this figure show that nanoparticles with encapsulated PZP give greater and more sustained antibody production over time than the standard pellet treatment currently being used.

DETAILED DESCRIPTION OF THE INVENTION

I. General Description

The prevention of microbial infections and pathogenic processes via the use of vaccines is considered one of the most effective and desirable procedures to combat illness. In this art, antigens or immunogens are introduced into an organism in a manner that stimulates an immune response in the host organism in advance of an infection or disease. As used herein, the term "antigen" or "immunogen" means a molecule that is specifically recognized and bound by an antibody. The molecule may be a protein or peptide of bacterial, fungal, protozoan, or viral origin, or a fragment derived from these antigens, a carbohydrate, or a carbohydrate mimetic peptide. The antigenic molecule(s) may also include self-antigens for the treatment of autoimmune diseases. Additionally, the antigenic molecule(s) may also include carbohydrates, nucleic acids, small organic molecules, or conjugates of any of these compounds. The specific portion of the antigen that is bound by the antibody is termed the "epitope".

The induction of an immune response depends on many factors, among which are believed to be the chemical composition and configuration of the antigen, the immunogenic constitution of the challenged organism, and the manner and period of administration of the antigen. An immune response has many facets, some of which are exhibited by the cells of the immune system (e.g., B-lymphocytes, T-lymphocytes, macrophages, and plasma cells). Immune system cells may participate in the immune response through interaction with an antigen or other cells of the immune system, the release of cytokines and reactivity to those cytokines. Immune response is conveniently (but arbitrarily) divided into two main categories—humoral and cell-mediated. The humoral component of the immune response includes production of antibodies specific for an antigen. The cell-mediated component includes the generation of delayed-type hypersensitivity and cytotoxic effector cells against the antigen.

Polymerized nanoparticles can be readily used in conjunction with synthetic vaccines. Individual "small" antigens, especially small peptides or carbohydrates, are difficult to administer and generally fail to elicit an effective immune response due to the hapten-related size issues. Thus, combining multiple copies of an antigen into a multivalent display enhances the immuno-recognition by the host, particularly human beings and commercially important livestock and other animals.

In addition, immunizations with multivalently displayed antigens can be improved by including targeting molecules or adhesins to direct the nanoparticle to the appropriate immune cell or location. A necessary step in the successful colonization and, ultimately, production of disease by microbial pathogens is the ability to adhere to host surfaces. This fundamental idea has led to an enormous amount of research over the last two decades that deals with understanding how pathogens target and adhere to host cells (Finlay, et al., "Common Themes in Microbial Pathogenicity Revisited," *Micro. Molec. Biology Rev.* 61(2): 136-169 (1997), which is hereby incorporated by reference in its entirety). Examples of such molecules which target mucosal epithelium include the tetanus toxoid; P pili of *E. coli*; type IV pili of *Pseudomonas aeruginosa, Neisseria* species, *Moraxella* species, EPEC, or *Vibrio cholerae*; fimbrial genes and several a fimbrial adhesins, including FHA, pertactin, pertussis toxin and BrkA of *Bordetella pertussis*; and SipB-D of *Salmonella typhimurium* (Finlay, et al., "Common Themes in Microbial Pathogenicity Revisited," *Micro. Molec. Biology Rev.* 61(2): 136-169 (1997), which is hereby incorporated by reference in its entirety); and the adenovirus adhesin (Gallichan, et al., "Mucosal Immunity and Protection after Intranasal Immunization with Recombinant Adenovirus Expressing Herpes Simplex Virus Glycopritein B," *J. Infect. Dis.* 168:622-629 (1993), which is hereby incorporated by reference in its entirety); or the Reovirus sigma-1 protein which targets the M-cell (Wu, et al., "M Cell-Targeted DNA Vaccination," *PNAS* 98(16):9318-9323 (2001), which is hereby incorporated by reference in its entirety); among other targeting molecules or adhesins.

The majority of the infections are caused by pathogens that first contact and then either colonize or cross mucosal surfaces to infect the host. It is possible to prevent the initial infection at mucosal surfaces by stimulating production of secretory IgA (S-IgA) antibodies directed against relevant virulence factors. S-IgA may prevent the initial interaction of the pathogen with the mucosal surface by blocking attachment and/or colonization, neutralizing surface acting toxins, or even inactivating invading viruses inside of epithelial cells.

Mucosal immunization may be an effective means of inducing not only S-IgA but also systemic antibody and cell-mediated immunity (Ghee, et al., "New Perspectives in Vaccine Development: Mucosal Immunity to Infections," *Infect. Agents Dis.* 2(2): 55-73 (1993) and Cardenas, et al., "Oral Immunization Using Live Attenuated *Salmonella* spp. as Carriers of Foreign Antigens," *Clin. Microbiol. Rev.* 5(3):328-342 (1992), which are hereby incorporated by reference in their entirety). While mucosal vaccination is attractive for inducing a variety of immune responses, mucosally administered antigens are frequently not immunogenic and require an adjuvant. *E. coli* heat-labile enterotoxin holotoxin (LT) and *Vibrio cholerae* enterotoxin (CT) represent promising mucosal adjuvants (Holmgren, et al., "Cholera as a Model for Research on Mucosal Immunity and Development of Oral Vaccines," *Curr. Opin. Immunol.* 4(4): 387-391 (1992), which is hereby incorporated by reference in its entirety). These adjuvants can be used to promote the production of serum and/or mucosal antibodies as well as cell-mediated immune responses against co-administered antigens.

Derived from the cell wall of *Salmonella* Minnesota, MPL adjuvant has proven ability to boost the potency of modern vaccines. This adjuvant may be a key component of vaccines using technologies such as recombinant and synthetic antigens. While vaccines incorporating these antigens are safer than previous attenuated or killed whole-cell vaccines, many of them are poorly immunogenic in the absence of a potent adjuvant. MPL adjuvant has demonstrated utility with peptide, bacterial sub-unit and synthetic polysaccharide antigens. Humoral, cell mediated and mucosal immunity can be stimulated by altering formulations and delivery routes.

Incorporation of the above mentioned adjuvants into the nanoparticle surface array, intercalation into the nanoparticle wall or encapsulation into the nanoparticle interior may provide an effective means of delivering to and stimulating the mucosal immune system to produce either or both humoral or cellular mucosal immunity to nanoparticle delivered antigens. As used herein the term "adjuvant" means any material which modulates to enhance the humoral and/or cellular immune response.

As used herein, the terms "displayed" or "surface exposed" are considered to be synonyms, and refer to antigens or other molecules that are present (e.g., accessible to immune site recognition) at the external surface of a structure such as a nanoparticle. From the targeted nanoparticle vaccines, we can expect highly intense, anamnestic and long-lasting immune responses (several years). Thus, the nanoparticle multivalency and targeting enhance the antigen concentration and promote delivery that favors the formation of high-affinity Th/B cell collaborations needed for optimal induction of the antibody response.

Phage display library technology is currently being used to discover many interesting peptide ligands that have immunogenic properties. However, a limitation of that technology is in recreating the conformational characteristics of the identified peptide to be similar to the viral capsid display platform. In many cases, the single, monomeric, synthetic peptide sequence fails to fold in the three-dimensional architecture or recreate a multi-peptide strand conformation that was present on the multivalent phage display. However, reassembling them in multivalent form amidst specific matrix lipid formulations on polymerized nanoparticle vaccines, such as in the present invention, often can restore the immunological activity of such peptides that have been isolated from the phage library.

Nanoparticle vaccines of the present invention are important new forms of drugs and drug delivery systems because the presentation of multivalent or aggregated antigens on the nanoparticle surface can enhance the desired immune response of a treated host. As used herein, the term "multivalent" means that more than one copy or type of antigen is displayed on a nanoparticle, preferably via linkers attached to component lipid monomers. Moreover, the one or more copies or types of antigen may be attached to the nanoparticle through two separate linkers, or may be attached to the nanoparticle via a common linker.

Arranging multiple copies of an antigen on a carrier and presenting them spatially is often more stimulatory than dispersed or solute molecules. The displayed antigens are able to bind more effectively to immune sites in the living body, thereby engaging more cell surface molecules on the specialized cells and antigen processing receptors involved in generating immune responses. As used herein, the term "antigen processing receptor" refers to receptors that mediate the uptake and processing of antigens, and then present the antigens for the development of immunity. Such receptors may be found on, for example, M-cells, dendritic cells and macrophages. Multivalent antigens have the advantage of increasing the desired immune response. Additionally, combinations of different antigens can be displayed on the same nanoparticle for purposes of eliciting a stronger immune response against one pathogen or against multiple pathogens at one time. It is envisioned that the specific display parameters important for protective efficacy against a specific disease or pathogen may vary.

Appropriate antigens for use with this vaccine technology may be derived from, but not limited to, pathogenic bacterial, fungal, or viral organisms, *Streptococcus* species, *Can-* dida species, *Brucella* species, *Salmonella* species, *Shigella* species, *Pseudomonas* species, *Bordetella* species, *Clostridium* species, Norwalk virus, *Bacillus anthracis*, *Mycobacterium tuberculosis*, human immunodeficiency virus (HIV), *Chlamydia* species, human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, cancer cells, or mixtures thereof Other appropriate molecules incorporated in the nanoparticle vaccines may include self-antigens, adhesins, or surface exposed cell signaling receptors or ligands. A variety of diseases and disorders may be treated by such nanoparticle vaccine constructs or assemblies, including: inflammatory diseases, infectious diseases, cancer, genetic disorders, organ transplant rejection, autoimmune diseases and immunological disorders.

T-cell activating molecules and/or adjuvants may be co-displayed or encapsulated with antigen(s) to direct the nanoparticle vaccine to a particular in vivo location or to enhance a certain desired immune response. Similarly, the addition of a targeting agent or agents to such nanoparticles provides the ability to direct such vaccines to a specific in vivo location, which increases the efficiency and effectiveness of a desired immune response. Targeted delivery to a specific site maximizes vaccine response and efficiency and minimizes potential side effects.

As used herein, the term "liposome" is defined as an aqueous or aqueous-buffered compartment enclosed by a lipid bilayer (Stryer, *Biochemistry*, 2nd Edition, W. H. Freeman & Co., p. 213 (1981), which is hereby incorporated by reference in its entirety). In general, liposomes can be prepared by a thin film hydration technique followed by a few freeze-thaw cycles. Liposomal suspensions can also be prepared according to methods known to those skilled in the art, for example, as described in U.S. Pat. No. 4,522,811 to Eppstein, et al., which is hereby incorporated by reference in its entirety.

As used herein, the term "nanoparticle" means a polymer sphere or spheroid that can be formulated to have a regular arrayed surface of defined, linked molecules in the nanometer size range (about 20 nm to 500 nm). Preferably, self-assembling monomers are utilized to form the nanoparticles.

In the nanoparticle vaccine constructs of the present invention, antigen(s) and/or targeting molecule(s) may be conjugated to individual monomeric lipid units and combined into self-assembling spheroid particles of a predetermined size. The nanoparticle chemistry allows nearly any type of immunogenic antigen to be attached to the particle surface, including proteins, peptides, carbohydrates, nucleic acids, small organic molecules, self-antigens, or conjugates of any of these compounds. The lipid monomer and a displayed molecule are conjugated, either covalently (via a tether or other linker moiety) or by complexing (either ionic or non-ionic), depending on the nature of the molecule being displayed.

Alternatively, conjugating molecules to the surface of a preformed nanoparticle is also encompassed by this invention. A linker or spacer molecule may also be used in conjugating antigen or other molecules to the nanoparticle. As used herein, the terms "linker" or "spacer" mean the chemical groups that are interposed between the nanoparticle and the surface exposed molecule(s). Preferably, linkers are conjugated to the surface molecule at one end and at their other end to the nanoparticle.

The hollow interior of the nanoparticles of this invention can be used to deliver antigen or antigens to the cells or tissues of interest. The release rate of such encapsulated antigen(s) can be modulated, for example, by varying the degree of polymerization of a liposome, by synthesizing the nanoparticle with some proportion of enzymatically degradable lipids, or by other means of altering the "leakiness" of the nanoparticle, as is known in the art.

The lipid monomers are typically selected from the group consisting of fatty acids containing 8-30 carbon atoms in a saturated, monounsaturated, or multiply unsaturated form. Furthermore, the lipid monomers may be acylated derivatives of polyamino, polyhydroxy, or mixed aminohydroxy compounds; glycosylacylglycerols; sphingolipids; steroids; terpenes; prostaglandins; non-saponified lipids; and mixtures thereof. The lipid monomers can also be diacetylene containing compounds.

The lipid monomers are polymerized, according to techniques known in the art, in order to provide stability and a certain rigidity to the constructs. As used herein, the term "polymerized" or "polymerization" encompass any process that results in the conversion of small molecular monomers into larger molecules consisting of repeated units. Typically, polymerization involves chemical crosslinking of molecular monomers to one another by exposure to UV light or other polymer-promoting catalysts.

As used herein, the term "polymerized liposome" means a liposome in which the constituent lipids are covalently bonded to each other by intermolecular interactions. The lipids can be bound together within a single layer of the lipid bilayer (the leaflets) and/or bound together between the two layers of the bilayer. Polymerizing the bilayer structure makes the assembly dramatically more resistant to enzymatic breakdown by acids, bile salts or enzymes present in the gastrointestinal tract compared to conventional, phosphotidylcholine-based liposomes. Similarly, the macromolecular nature of the nanoparticles covered with surface targeting or other small molecules can retard some of the physiological degradative pathways which would ordinarily degrade such molecules.

Non-polymerized liposomes have been used to change the pharmacodynamics of therapeutic substances either encapsulated inside their structures or displayed on their surfaces. Entrapment of sensitive molecules within the nanoparticle can shield the material from such degradative processes. This is an important aspect of the present invention when considered in its antigen-delivery embodiments. The demonstration of this principal has been described and is known in the art with regard to conventional bilayer liposomes. The escape rate of the encapsulated drug is largely controlled by the lipophilicity of the drug or its solubility in the lipid membrane.

Polymerized liposome nanoparticles, on the other hand, can be formulated with a defined "leakiness" by having pores of an optimal size, by making the nanoparticles with specific ratios of enzymatically degragdable lipids. In this way, engineering the encapsulating nanoparticle can modulate the optimal escape rate of any antigen at immune uptake sites, and techniques to modulate leakiness and escape or release rates also are known in the art.

II. Specific Embodiments

The vaccine system of the present invention is versatile, as the presentation of multiple and different antigens provides for immunization for several different and distinct infective stimuli. For example, a single vaccine prepared in accordance herewith may present antigens for more than one bacterial, viral, or fungal species to elicit immune responses to each of these distinct stimuli. Additionally, T-cell directing peptides along with carbohydrates or peptides as antigens can be incorporated into the particle to facilitate humoral and cellular immunity to such antigens.

The spheroid assembly of the nanoparticle vaccine carrier of the present invention is easy to construct and functionalize. It is polymerized to be "rigid", not suffering from the folding uncertainties associated with soluble linear or branched chain polymers, and unlike conventional liposomes, they are inert toward random fusion with themselves or other membranes. These carriers resemble a very simplified bilayer surface and as such, allow the recognition elements to be varied and investigated systematically.

In general, it will be readily appreciated that the practice of this invention is not critically dependent on the chemical details of the composition. The practitioner is free to assemble the composition according to a number of different approaches. Variations in polymerization chemistry and the conjugation of antigens, adjuvants, and/or targeting molecules are permitted and included in the scope of this invention. Additionally, combining the techniques described herein to create a combination nanoparticle vaccines with molecules both encapsulated and surface displayed (exterior or interior) is included in the scope of this invention.

Designing particular linkages between the displayed molecules and lipid monomers also is well within the skill of the ordinary practitioner. The optimization of such linkages and compounds may be achieved by routine adjustment and following the effects of adjustment on immune response in one of many techniques established in the art.

The following description and examples are provided merely as an illustration of possible approaches and preferred embodiments. Persons skilled in the art will readily understand that various modifications may be made according to the teachings herein.

Preparation of Nanoparticle Vaccines Having Surface-exposed Molecule(s) and/or Targeting Molecule(s):

When assembling nanoparticles according to embodiments of the present invention, which have surface displayed antigen or types of antigen and/or targeting molecules, two strategies are employed to display virtually any molecule or protein multivalently. Depending upon the kind of molecule and its sensitivity to nanoparticle formulation conditions, either the antigen(s) and/or target molecules are preconjugated to a polymerizable lipid or the nanoparticle is pre-formed and conjugation of the surface-exposed molecules is conducted as a final step. While it is not critical that particular surface exposed molecules always be chosen with respect to particular receptors, it is important that at least one molecule type specifically interacts with (or binds to) a receptor that leads to antigen processing, and that at least one molecule type is therefore capable of eliciting a protective immune response.

A certain proportion of the lipid monomers in the nanoparticle are attached to the antigen and a distinct proportion of the lipids in the nanoparticle are attached to a second type of antigen or targeting molecule that is different from the first molecule type. It is important to note that the different types of molecules are displayed in a randomly generated regular array on the nanoparticle carrier. In effect, the antigen processing receptor(s) or targeting molecule binding receptor(s) readily accept those multivalently displayed units formed by first and second (or more) displayed molecule pairs that have the optimal spacing and charge/hydrophobicity characteristics. The preferred embodiments of the invention are produced according to the methods described herein, in which the relative amounts and respective ratios of the lipid monomers bearing different display molecules as well as spacer monomers are determined empirically.

Surface-exposed molecules (antigens and/or targeting molecules) may be conjugated or complexed to the nanoparticle using any means known in the art. The term "conjugated" refers to molecules that are covalently bound to each other through one or more linker molecules; whereas the term "complexed" refers to molecules that are non-covalently bound to each other through one or more linker molecule.

For instance, surface-exposed molecules may be conjugated to a lipid using an appropriate linker. The term "linker" refers to a compound that is capable of covalently binding two molecules together. Linking may be performed with either homo- or heterobifunctional agents, i.e., SPDP, DSS, SIAB.

Methods for linking are disclosed in PCT/DK00/00531 (WO 01/22995) to deJongh, et al., which is hereby incorporated by reference in its entirety. Such methods may generally include the steps of:

a) reacting an antigen or immunogen with a reactive linker end thereby producing a mixture of linker derivatives of the antigen(s);

b) isolating the antigen derivatized with a single linker residue, c) activating the isolated linker derivative of the antigen, d) reacting the activated linker derivative of the antigen with the lipid thereby producing conjugates between the antigen and the lipid monomer.

Note that the above steps may be conducted with the addition of the targeting molecule(s) attached to a lipid in the cases where targeted vaccines are desired.

In one embodiment, the first linker is a bifunctional linker (i.e., with two functional groups), preferably a heterobifunctional linker (i.e., with two different functional groups). In a further embodiment, the linker is selected from the non-limiting group consisting of N-succinimidyl (4-iodoacetyl) aminobenzoate (SIAB), N-succinimidyl-3-(2-pyridylthio) propionate (SPDP), N-succinimidyl S-acetylthioacetate (SATA), m-maleimidobenzoyl-N-hydroxysuccinimide ester (MBS) and N-g-maleimidobutyryloxy-succinimide ester (GMBS). In a further embodiment, the linker is Traut's Reagent 2-iminothiolane in combination with SPDP. In still a further embodiment the linker is succinmidyl dicarbonyl pentane or disuccinimidyl suberate. In a further embodiment, the linker is selected among those disclosed in The Pierce Products Catalogue (Pierce Chemical Company, USA) and the Double Agents™ Cross-Linking Reagents Selection Guide (Pierce Chemical Company), which are herein incorporated by reference.

In the general method presented above, any suitable method may be used to purify the linker derivatized attachment molecule. For instance, the linked attachment molecule may be purified by preparative reverse phase HPLC (RP-HPLC). In another embodiment, the linked attachment molecule may be purified by membrane filtration, such as ultrafiltration or diafiltration. Unreacted linker may be removed by size exclusion chromatography, such as gel filtration, or equilibrium dialysis. The final conjugate may also be purified using any suitable means, including for instance gel filtration, membrane filtration, such as ultrafiltration, or ion exchange chromatography, or a combination thereof.

Molar ratios to be used in linking methodology may be readily optimized by those of skill in the art, but generally will vary between about 1:1 to about 5:1 linker to attachment molecule depending on the linker and the efficiency of linking reaction. The ratio of linked antigen(s) to lipid may also be readily optimized by those of skill in the art, but will generally range from about 1:1 to about 10:1 lipid to antigen.

Alternatively, surface-exposed molecules may be complexed with a lipid using an appropriate complexing agent. The term "complexing agent" refers to a compound that is capable of non-covalently binding two molecules together. Complexes may be formed between a 6× His tag on one molecule and a nitrilotriacetic acid-metal ion complex on the other molecule.

Additionally, peptide and protein antigens may be expressed as fusion proteins operably linked to the lipid. Fusion proteins are known in the art, such as those disclosed in Yu et al., "The Biologic Effects of Growth Factor-Toxin Conjugates in Models of Vascular Injury Depend on Dose, Mode of Delivery, and Animal Species," *J. Pharm. Sci.,* 87(11):1300-4 (1998); McDonald et al., "Large-Scale Purification and Characterization of Recombinant Fibroblast Growth Factor-Saporin Mitotoxin," *Protein Expr. Purif.,* 8(1):97-108 (1996); Lappi et al., "Expression and Activities of a Recombinant Basic Fibroblast Growth Factor-Saporin Fusion Protein," *J. Biol. Chem.,* 269(17):12552-8 (1994); Wu et al., "Gene Transfer Facilitated by a Cellular Targeting Molecule, Reovirus Protein σ 1," *Gene Therapy,* 7:61-69 (2000); and Prieto et al., "Expression and Characterization of a Basic Fibroblast Growth Factor-Saporin Fusion Protein in *Escherichia coli,*" *Ann. N Y Acad. Sci.* 638:434-7 (1991), all of which are hereby incorporated by reference in their entirety. By way of example, fusion-derived immunogen conjugates include K99 fimbrial protein from bovine enterotoxigenic *E. coli* fused to protein σ 1, colonization factor antigen 1 fimbrial protein from human enterotoxigenic *E. coli* fused to protein σ 1, or myelin basic protein fused to protein σ 1.

FIG. 1 depicts several of the conjugations scenarios which may be used to attach a variety of molecular classes to the nanoparticle vaccine carriers of this invention. By incorporating a water-soluble linker between lipid and antigen or target molecule, a great range of flexibility is allowed for the tethered linker. Such linker length may range from one atom to several hundred.

Once the antigen(s) and/or target molecule(s) are conjugated to lipid, the nanoparticle can be formed by mixing the lipid with other polymerizable spacer or matrix lipids. By controlling the amounts of target lipid to matrix lipid incorporated into the nanoparticle formulation, the density of the surface array of molecules can be varied. In this way, the optimal density of antigen(s) and/or target molecules leading to the highest biological activity can be determined. Similarly, the effectiveness of a drug or toxin may also be optimized.

The matrix lipid can be charged or uncharged to impart a surface of electronically neutral or specific charge around the target molecule (as shown in FIG. 2). Charged lipids can be readily synthesized by attaching functional moieties, such as an $SO_4$ molecule to the head group, which would, in this case, result in a negative charge. Methods of synthesizing variously charged lipids are further described in U.S. Pat. No. 6,235,309 to Nagy, et al. and Bruehl, et al., "Polymerized Liposome Assemblies: Bifunctional Macromolecular Selectin Inhibitors Mimicking Physiological Selectin Ligands," *Biochem.* 40:5964-5974 (2001), which are hereby incorporated by reference in their entirety. The surrounding charge, positive or negative (or neutral) can play a dramatic role in the overall biological activity of the nanoparticle carrier.

Methods for polymerized nanoparticle preparation are disclosed in U.S. Pat. No. 6,235,309 to Nagy, et al., which is hereby incorporated by reference in its entirety. Such methods may generally include the steps of a) mixing a desired molar percentage of antigen-lipid (and/or targeting-lipid) with a desired molar percentage of matrix lipid;

b) evaporating the stock solvent(s) under vacuum and adding a desired amount of water or buffer to create a desired concentration of lipid suspension;

c) agitating the suspension by probe sonication or other sonication method to promote the lipids to self-assemble into uni- or multi-lammelar liposome structures. Alternatively, the lipid suspension can be pressed through a membrane or orifice of defined pore size to produce extruded liposomes of a desired size range;

d) the pre-polymerized liposomes are cooled and caused to polymerize by UV light exposure or other polymer-promoting catalysts.

By varying the amount of crosslinking of the lipid monomers during the polymerization process, different degrees of polymerization, and therefore different degrees of rigidity, may be obtained. This may be useful for specific display characteristics (i.e., spatial orientation) desired for presented antigen(s) and/or target molecule(s) or to allow for resistance or susceptibility of the nanoparticle to enzymatic or other degradative pathways or processes. The degree of crosslinking in the polymerized liposomes preferably ranges from about 30 to 100 percent (i.e., up to 100 percent of the available bonds are made).

Alternatively, the nanoparticle can be formed with reactive conjugation groups decorating the surface. This technique will obviously be successful only if the conjugation groups are compatible with the polymerization conditions in an aqueous environment. If the groups are unaffected by polymerized nanoparticle formation, simple incubation with the reactive antigen or target molecule will affect the conjugation, as schematically depicted in FIG. 3.

Preparation of Nanoparticle Vaccines Having Encapsulated Antigen(s):

To encapsulate antigen the nanoparticle is constructed in a media that contains a suitably high concentration of the soluble antigen. Because the nanoparticle has an aqueous compartment fully surrounded by a polymer membrane the resulting antigen concentration on the inside of the nanoparticle will be equal to that of the bulk media surrounding the nanoparticle. The non-encapsulated antigen can be removed from the nanoparticle solution by either size exclusion chromatography or equilibrium dialysis. Once the non-encapsulated antigen is removed, the polymerized nanoparticles can be prepared and purified by any suitable method discussed in the above example, with the resulting nanoparticle as depicted in FIG. 4.

EXAMPLES

Example 1

Liposome Preparation.

Polymerized polydiacetylene (PDA) liposomes were prepared according to the method described by Spevak, et al., "Carbohydrates in an Acidic Multivalent Assembly: Nanomolar P-Selectin Inhibitors," *J. Med. Chem.,* 39(5):1018-1020 (1996), which is hereby incorporated by reference in its entirety. Briefly, polymerizable lipids and antigen- or targeting-lipids were mixed and evaporated to a film. Deionized water was added to the films to give a 1 mM (total lipid) suspension. The suspension was heated to between 70-80° C. and probe sonicated for 30 min. The resulting clear solution was then cooled to 5° C. for 20 min. and polymerized by UV light irradiation (254 nm). The deeply colored solutions were syringe filtered through 0.45 µm or 0.2 µm cellulose acetate filters in order to remove trace insoluble aggregates. Essentially all of the lipid material (>98%) is incorporated into the soluble liposomes. In the case of carbohydrate-displaying nanoparticles, Dionex Analysis (Glyko, Inc., Novato, Calif.) quantitatively determined the carbohydrate contents in the polymerized liposome assemblies. The polymerized liposome preparations containing carbohydrate were digested with 2N HCl for 2 hrs. at 100° C. The solution was dried after freezing by Speedvac, the residue was redissolved in a known volume of water and the solution was centrifuged to separate the polymer particles. An aliquot was injected into the Dionex instrument for monosaccharide identification and quantification. The monosaccharides were identified by comparison to D-galactose and L-fucose standards. Each sample was run in duplicate.

Example 2

*Candida albicans* Glycoprotein Presentation on Nanoparticles for Use as a Vaccine.

Glycoproteins from the cell wall of *Candida albicans* are highly mannosylated, phosphomannoprotein complexes that are weak immunogens when administered alone or with adjuvants (CFA, Ribi RS-700, etc), but conjugation to a carrier protein like BSA or encapsulation in traditional liposomes elicits increased immune responses that protect mice against disseminated and mucocutaneous candidiasis (Han, et al., "Antibody Response that Protects Against Disseminated Candidiasis," *Infect. Immun.* 63:2714-2719 (1995); Han, et al., "A Vaccine and Monoclonal Antibodies that Enhance Mouse Resistance to *Candida albicans* Vaginal Infection," *Infect. Immun.* 66:5771-5776 (1998); and Han, et al., "*Candida albicans* Mannan Extract-Protein Conjugates Induce a Protective Immune Response Against Experimental Candidiasis," *J. Infect. Dis.* 179:1477-1484 (1999); which are hereby incorporated by reference in their entirety). Vaccine formulations for the *Candida* glycoproteins in multivalent display on polymerized nanoparticles promoted protective immune responses against disseminated candidiasis, as shown below.

Glycoprotein components (phosphomannoprotein complexes) were isolated from the *Candida albicans* cell wall by extraction using 2-mercaptoethanol (2-ME) and the carbohydrate content established as described previously (Kanbe, et al., "Evidence that Mannans of *Candida albicans* are Responsible for Adherence of Yeast Forms to Spleen and Lymph Node Tissue," *Infect. Immun.* 61:2578-2584 (1993), which is hereby incorporated by reference in its entirety). The phosphomannoprotein extract (11 mg) was derivatized by reaction with N-(2,3-epoxypropyl)phthalimide (4 mg) in water at pH 11. After treatment by aqueous hydrazine the amine-derivatized phosphomannan (3.5 mg) was reacted with the NHS ester of 10,12-pentacosadiyneoic acid (PCDA, 189 mg) in DMF. The resulting lipid conjugated phosphomannan compound was purified by trituration with chloroform and methanol. The phosphomannan-lipid (0.6 mg) was added to variously charged (anionic COOH, anionic $SO_3$, cationic $NH_2$, or neutral OH) PCDA (5.5 mg) in water (pH 7) to give bilayer liposomes, after 30 min. sonication. The liposomes were polymerized by exposure to UV light for approx. 5 min. The highly colored polymerized nanoparticles were sterile filtered (0.2 u) and assessed for the presence of endotoxin by the *Limulus* Amebocyte Lysate test (results indicated <3.8 EU/ml) prior to use. The vaccine potential of the resulting *Candida* glycoprotein-nanoparticles were evaluated in vivo as described below.

Immunization and live *Candida* challenges were performed in mean survival time (MST) studies as summarized in Table 1:

TABLE 1

| Item | Details |
|---|---|
| Mice | 5-6 week old BALB/c females |
| | 5 mice per treatment group (included Dulbecco's Phosphate Buffered Saline (DPBS) and adjuvant only controls) |
| Candida Glycopeptide Nanoparticles | JN#5-100-1 (matrix lipid = Anionic COOH) |
| | JN#5-100-2 (matrix lipid = neutral OH) |
| | JN#5-100-3 (matrix lipid = Anionic $SO_3$) |
| | JN#5-100-4 (matrix lipid = Cationic $NH_2$) |
| Immunizations i.p. route | Day 0 - Complete Freund Adjuvant (CFA) with priming dose of each nanoparticle formulation above. Doses were administered based on a 40 µg carbohydrate equivalent; Other groups received CFA alone or DPBS alone |
| | Day 21 - Incomplete Freund Adjuvant (IFA) with boost dose (same as above) or adjuvant or buffer alone |
| | Day 28 - live *Candida* yeast challenge 5 × $10^5$ colony forming units (cfu)/mouse m 0.2 ml DPBS given i.v., followed by twice daily monitoring of severe disease indicators and survival |
| C. albicans: | C. albicans strain CA-1 grown as hydrophilic yeast cells (stationary phase growth in glucose yeast extract peptone medium at 37° C.), |

The MST results (FIG. 5) show that certain vaccine formulations of the *Candida* glycopeptide nanoparticles elicited significant protection against candidiasis compared to adjuvant and buffer only control groups. The majority of mice (4/5) immunized with the anionic COOH formulation (JN#100-1) of *Candida* glycopeptides survived 55 days, whereas there were no survivors in other treatment groups after 15 days.

The results show that some glycopeptide-nanoparticle formulations were protective while others were not, indicating that the presentation context of the immunogen plays a crucial role in generating protective responses. Each glycopeptide-nanoparticle formulation contained the same molar concentration glycopeptide-lipid mixed with different matrix lipid prior to polymerization. The resulting preparations contained the same amount of total immunogen, but surface displayed in differently charged environments established by the various matrix lipids. The ability to elicit protective immune responses with the *Candida* glycoproteins depended on weak anionic display context for the immunogen.

Compared to previous immunizations with traditional liposomal formulations of the *Candida* glycoproteins requiring 5 or more immunization doses (Han, et al., "Antibody Response that Protects Against Disseminated Candidiasis," *Infect. Immun.* 63:2714-2719 (1995), which is hereby incorporated by reference in its entirety), the polymerized nanoparticles required fewer (2) doses to achieve significant protection against disseminated disease. Compared to previous immunizations with *Candida* glycoproteins conjugated to carrier protein (Han, et al., "*Candida albicans*

Mannan Extract-Protein Conjugates Induce a Protective Immune Response Against Experimental Candidiasis," *J. Infect. Dis.* 179:1477-1484 (1999), which is hereby incorporated by reference in its entirety, the polymerized nanoparticle formulations only consisted of antigenic determinants found in the *Candida* glycoprotein extract and did not contain heterologous antigens contributed by the carrier protein. Thus, the presentation of *Candida* glycoproteins by the polymerized nanoparticles overcame the general requirement for conjugation of poorly immunogenic carbohydrates to a carrier protein that provides the T-dependent antigenic help for generating effective immunity. Synthesis of the multivalent polymerized nanoparticle vaccine formulations with the *Candida* glycoproteins facilitated improved control of the display context and antigenic determinants necessary to induce protective immune responses against *Candida* antigens in vivo.

In other experiments, the *C. albicans* glycoproteins were conjugated to preformed polymerized nanoparticles and administered to mice. The alternate conjugation method also resulted in significant protective response against candidiasis (FIG. 6).

Example 3

*Candida albicans* Carbohydrate Antigen in Conjunction with T-Cell-Directing Peptides as Presented on a Nanoparticle.

As reflected in the biomedical literature, a vaccine approach based on small peptides or carbohydrates has remained somewhat limited. This is likely related to their low immunogenicity and the scarcity of adjuvants that can be used with them in humans. Generally, small molecules act as haptens that lack the necessary Th epitopes to stimulate an effective immune response. Conjugation of small peptides or non-protein epitopes to other proteins, liposomes or polymer carriers has proven to be useful in stimulating antibody responses in a number of systems. The carrier serves a dual function, in addition to polyvalent peptide presentation, because it can also display a Th epitope. Long-lasting and potent immune responses have been elicited by small peptides covalently conjugated to the surface of the vesicle additionally carrying an adjuvant such as monophospholyl lipid A or lipopeptides such as $Pam_3CAG$. Nanoparticle carriers that display separate B and Th epitopes can first target antigen-specific B-lymphocytes and, after uptake, the Th epitopes would then target intracellular MHC class II-containing compartments. Such a synthetic construct induced a highly intense, anamnestic and long lasting (>2 years) immune response, in mice.

Beta-1,2-linked mannosyl oligosaccharides similar to those found on the surface of *Candida albicans* were chemically synthesized (M. Nitz, et al., "Synthesis of a Beta-1,2-mannopyranosyl tetrasaccharide Found in the Phosphomannan Antigen of *Candida albicans*," *Organic Letters*, 2(19): 2939-2942 (2000), which is hereby incorporated by reference in its entirety) with an amine terminated linking arm. The oligosaccharides were reacted with the NHS ester of 10,12-pentacosadiyneoic acid in DMF. The resulting lipid conjugated oligosaccharide compounds were purified by silica gel chromatography with chloroform and methanol. The lipid-conjugated oligosaccharide was added to the T-cell directing peptide (tetanus toxin peptide: TT) TT-lipid in water (pH 7) plus the matrix lipid PCDA to give bilayer liposomes, after 30 min. sonication. The liposomes were polymerized by exposure to UV light for approx. 5 min. The highly colored polymerized nanoparticles were then sterile filtered (0.2 u) and used for biological evaluation.

Example 4

Immunogenicity Study of Control (Blank) Nanoparticle Formulation.

Control nanoparticles (JN#6-123-1) were prepared as examples without added antigen by mixing matrix lipids at a ratio of 25% sulfate and 75% hydroxyl groups followed by UV polymerization and sterile filtration. The control nanoparticles were utilized in preliminary immunization studies to determine background responses elicited against the particle materials.

Immunizations. Pre-immune serum samples were obtained from three BALB/c female mice (8-10 weeks old). Mice were given control sulfated nanoparticles (i.p. administration, 100 µl 12 mM JN#6-123-1, no adjuvant) and boosted with an equivalent dose on days 21, 35, and 49. Serum samples were collected via tail vein or saphenous vein bleeds on days 28, 42, and 56.

Enzyme Linked Immunosorbent Assay (ELISA) screening for total immunoglobulin (Igs) levels. Serial bleeds for each mouse were assessed for the level of total immunoglobulins (Igs) via a capture ELISA. Briefly, microtiter wells were coated with goat anti-mouse G+M+A, blocked with a skim milk/bovine serum albumin (BSA) block solution (5% non-fat milk and 1% w/v BSA in Tris-buffered saline containing 0.1% v/v Tween 20), washed and incubated with pre-immune or immune serum samples diluted in blocking buffer. Plates were washed, incubated with enzyme-conjugated secondary antibodies detecting total immunoglobulins (IgG+M+A), and then substrate added to determine the absorbance values. In parallel control ELISAs, other murine serum samples from immunizations with M13 virus clones were performed for quality control to insure that changes in Ig levels were detected when a known increase in specific antibody titers had occurred.

Preliminary ELISAs indicated that dilution of serum samples to approximately 1:160,000 facilitated on-scale absorbance readings for determination of total Igs levels. FIG. 7 Panel A shows the results of ELISAs tracking the total Igs in control nanoparticle immunized mice. Mice #1 and #2 show slight increases in antibody levels while total Igs levels for mouse #3 fluctuated and did not appear to correlate with the immunization regimen. The increases between pre-immune and subsequent bleeds for mice #1 and #2 are much less than what occurs for immunizations with a simple antigen, like the rising titers for IgG shown in FIG. 7 Panel B for serial samples from viral immunization.

Screening for nanoparticle-specific antibody responses. Evaluation of nanoparticle-specific antibody responses was performed by agglutination, filtration to remove adsorbed antibody, and by ELISA testing.

First, direct agglutination of the sulfated nanoparticles with the pre- and post immune serum samples was assessed visually and via fluorescent microscopy. Briefly, serum samples were diluted 1:5 in sterile phosphate buffered saline, mixed with an equal volume of the sulfated nanoparticles JN#6-123-1, incubated briefly and checked for agglutination. For fluorescent assessments, sample fields of view were placed under UV light excitation for 30 seconds and the image captured. Results indicated minimal if any increase in agglutination for immune serum samples compared to pre-immune control bleeds, except for the $3^{rd}$ bleed samples that were scored as weak 1+/− agglutination. These results indicate minimal to no specific antibody response reactive with the surface of the sulfated nanoparticles.

Second, total Igs levels were assessed before and after pre-adsorption of mouse #2 serum samples with sulfated nanoparticles or irrelevant nanoparticles. Briefly, pre- and post-immune serum samples were mixed with sulfated nanoparticles JN#6-123-1 or with an irrelevant peptide-nanoparticle JN#5-53-2 (displayed a 9-mer peptide, PS76 YRQFVT-GFW (SEQ ID NO: 1) in an 85% hydroxyl matrix lipid). The mixture samples were filtered across 0.02 μm membranes (pre-blocked with BSA and rinsed with sterile DPBS) to remove nanoparticles and the resulting filtrate assessed via total Ig ELISAs, as described above. The sulfated nanoparticles adsorbed a significant amount of antibody from the pre-immune serum (approx. 60% decrease) and similar (or slightly less) amounts adsorbed from the immune serum samples (approx. 52% for $1^{st}$ bleed, 57% for $2^{nd}$ bleed, and 43% for $3^{rd}$ bleed). The irrelevant PS76-nanoparticles showed variable, but less adsorption of antibody from mouse #2 samples. These results support a non-specific mechanism of antibody binding to sulfated nanoparticles and not adsorption of antibodies specifically reactive to the sulfated nanoparticle surface.

Third, microtiter wells were coated with sulfated nanoparticles JN#6-123-1 or an irrelevant nanoparticle and assayed for antibody binding in ELISA screens. The irrelevant controls for this assessment included a peptide-conjugated nanoparticle JN#5-53-2 (PS76 peptide—YRQFVT-GFW (SEQ ID NO:1) in an 85% hydroxyl matrix lipid) and irrelevant serum samples from mice immunized with a similar PS76-nanoparticle JN#5-85-3, which failed to produce peptide specific responses in that formulation.

Briefly, serum samples were diluted in block, incubated in the nanoparticle-coated wells, and processed as described above. Results (FIG. 8) show that very little if any specific antibody is generated against the corresponding nanoparticle preparation. In fact, the sulfated nanoparticle coated wells bound more antibody from all serum samples, including the serum samples from PS76-nanoparticle immunized mice. Taken together with the adsorption/filtration results, these observations suggest a non-specific mechanism of binding antibody that may be related to the anionic charge of the sulfated particles. There was minimal booster effect observed, which suggests a lack of specific immune responses. If there are specific antibodies being elicited against blank nanoparticle materials or even hapten-sized moieties conjugated to nanoparticles (e.g. the 9-mer PS76 peptide), then that level could not be distinguished from non-specific binding in these assays. These assays demonstrate the low immunogenicity of nanoparticle materials alone.

Example 5

Sigma Protein Displayed on Polymerized Nanoparticle for Targeting Antigen to the M-Cell.

Similar to the T-cell directing nanoparticles described in Example 3, nanoparticle vaccines may be formulated that display a different peptide (in this case, the sigma protein) on the surface of the nanoparticle to direct the vaccine to specifically target M-cells. In this way, surface antigens co-displayed with the sigma protein will be processed by the M-cell for a specific immune response. Likewise, material (such as antigen or DNA encoding an antigen) encapsulated inside an M-cell targeted nanoparticle essentially will be invisible to the immune system until taken into the M-cell and processed, resulting in a desired humoral and cell-mediated immune response.

This sigma-1 targeting adhesion molecule has been demonstrated to bind nasal associated lymphoid tissue (NALT) M cells (Wu, et al., "M Cell-targeted DNA Vaccination," *PNAS*, 98(16):9318-9323 (2001), which is hereby incorporated by reference in its entirety). A frozen section of normal murine BALB/c NALT was reacted with recombinant targeting adhesion and UEA-1, and was shown to not only bind to NALT M cells, and to localize within the M cell itself. Additionally, DNA (β-galacosidase) was expressed after delivery by this targeting molecule to mouse L cells, compared to a control, without the targeting molecule.

Example 6

Nanoparticle with Encapsulated PZP Glycoprotein as a Contraceptive Vaccine in Rabbits.

Porcine zona pellucida (PZP) is a glycoprotein found in the extracellular matrix surrounding oocytes and is important in fertilization and sperm recognition. It was found that monoclonal antibodies generated against this protein act as a short duration contraceptive in the treated animal. However, the duration of the protein in vivo make it necessary for the administrator to treat an animal multiple times per season to achieve year-long contraception.

PZP was encapsulated in polymerized nanoparticles and tested as a contraceptive vaccine in rabbits. A mixture of EAPDA (256 mg) and sulfo-EAPDA (107 mg) were sonicated for 30 min. in 4 ml of an aqueous solution of PZP (2.6 mg/ml). The PZP-encapsulating liposomes were polymerized by exposure to UV light for approx. 5 min. The highly colored polymerized nanoparticles were then sterile filtered (0.2 u) and dialyzed to remove any non-encapsulated PZP. The material was then biologically evaluated.

Rabbits were inoculated intramuscularly at two week intervals as follows:

a) Rabbit S (Antigen Prime Only): nanoparticles;

b) Rabbit N (Nanoparticle): PZP+modified Complete Freund Adjuvant (mCFA);

c) Rabbit AT (Pooled Ref Sera): PZP+mCFA and nanoparticles;

d) Rabbit E (Negative Control): mCFA.

The results of this study indicated a high and sustained antibody response in rabbits with a single injection of the PZP-nanoparticles, having encapsulated effective dosages of PZP in combination with adjuvant, that are comparable to that of the twice injected PZP positive control (FIG. 9).

Example 7

Nanoparticle with Encapsulated PZP Glycoprotein as a Contraceptive Vaccine in Horses.

PZP glycoprotein was also encapsulated in nanoparticles and administered to horses as a contraceptive vaccine. As described in Example 5, a mixture of EAPDA (256 mg) and sulfo-EAPDA (107 mg) were sonicated for 30 min. in 4 ml of an aqueous solution of PZP (2.6 mg/ml). The PZP-encapsulating liposomes were polymerized by exposure to UV light for approx. 5 min. The highly colored polymerized nanoparticles were then sterile filtered (0.2 u) and dialyzed to remove any non-encapsulated PZP. The material was then biologically evaluated.

The horses were wild but in captivity. Twenty mares were divided into treatment groups as follows (treatments were all given intramuscularly):

1) 65 μg PZP emulsified in 0.5 ml Complete Freund Adjuvant (CFA)+100 μg PZP encapsulated in nanoparticles;

2) 200 μg PZP incorporated in lactide-glycolide pellets.

Nanoparticles with encapsulated PZP showed greater and more sustained antibody production over time than the other treatments tested, including the contraceptive currently being used (pellets) (FIG. 10).

Example 8

Protective Antibody Response from Nanoparticle Vaccine Displaying Group B Streptococcal Antigens.

Group B streptococci (GBS) are a major cause of neonatal sepsis and meningitis. GBS are one of many examples of microbial polysaccharides that are notably poor immunogens. Efforts to prevent this disease using GBS carbohydrates are marginally effective in eliciting antibody or a protective immune response. Immunogenic peptide mimics of the type III capsular carbohydrate of GBS have been developed (Pincus, et al., "Peptides that Mimic the Group B Streptococcal Type III Capsular Polysaccharide Antigen," *J. Immunol.*, 160(1):293-298 (1998), which is hereby incorporated by reference in its entirety). The murine mAb S9, a protective antibody against the type III capsular polysaccharide of GBS was used to select epitope analogues from the J404 peptide display phage library. Two populations or phage were identified with displayed sequences of WEN-WMMGNA (SEQ ID NO:2) and FDTGAFDPDWPA (SEQ ID NO:3). Display of these immunogenic peptide mimics of the GBS carbohydrate on polymerized nanoparticles, possibly with targeting molecules, would elicit an efficient and effective immune response. Similarly, display of peptide mimetics of the other GBS carbohydrate types (i.e., Ia, Ib, II and V) on a nanoparticle would likewise result in a desired immune response against CBS.

Example 9

Nanoparticle Vaccine Against Anthrax.

Anthrax produced by the bacterium *Bacillus anthracis* is an infectious disease resulting from contact with endospores in contaminated animal products or their dusts. Cutaneous anthrax, which accounts for 95% of cases in the world, results from contamination of a lesion in the skin and progresses to fatal septicemia in 10-20% of untreated cases. Inhalation anthrax is nearly always lethal without early, aggressive intervention. In the results of a field study with the U.S. military, use of the currently available anthrax vaccine, Anthrax Vaccine Adsorbed (AVA), suggested that it prevented cutaneous infection in humans (Demicheli, et al., "The Effectiveness and Safety of Vaccines Against Human Anthrax: A Systematic Review," *Vaccine*, 16(9-10):880-884 (1998), which is hereby incorporated by reference in its entirety). This vaccine has been shown to protect monkeys from inhalation anthrax, but is fraught with inadequacies and problems, including mysterious side effects, frequent immunization schedule, painful subcutaneous delivery, outdated design, and short shelf life (Vastag, "Medical News & Perspectives: Despite Finding Anthrax Vaccine Useful, IOM Recommends Seeking a Better One," *JAMA*, 287(12):1516-1517 (2002), which is hereby incorporated by reference in its entirety). Clearly, a new vaccine is needed.

Work is currently in progress with regard to determination of specific peptide mimic antigens which are effective in eliciting an effective immune response against anthrax toxin. Preparation of an effective vaccine against anthrax, especially inhalation anthrax, could be prepared by displaying immunogenic antigen against anthrax toxin on a nanoparticle in combination with B or Th epitopes as described in Example 3. Such a presentation would elicit a broad and long-term immune response against anthrax toxins.

Example 10

The Generation of Mucosal Tolerance Using M-Cell Delivery of Nanoparticle Vaccine Displaying Antigens Which Promote Anergy to Self-Antigens.

Autoimmune diseases such as arthritis (7 different types), multiple sclerosis, uveitis, myasthenia gravis, type 1 diabetes, thyroiditis and colitis respond favorably to the oral delivery of native proteins, sometimes peptides, associated with the tissue under attack by the immune system (Cohen, "T Lymphocyte Clones and Experimental Autoimmune Diseases," *Behring. Inst. Mitt.*, 77:88-94 (1985), which is hereby incorporated by reference in its entirety). This phenomenon, referred to as oral tolerance, interrupts and suppresses the autoimmune disease process by stimulating the natural mucosal immune mechanisms in the gut associated lymphoid tissues (GALT) of the small intestine (Hanninen, "Prevention of Autoimmune Type 1 Diabetes Via Mucosal Tolerance: Is Mucosal Autoantigen Administration as Safe and Effective as it Should Be?," *Scand. J. Immunol.*, 52(3): 217-225 (2000); Shi, et al., "Mechanisms of Nasal Tolerance Induction in Experimental Autoimmune Myasthenia Gravis: Identification of Regulatory Cells," *J. Immunol.* 162(10): 5757-5763 (1999); Hafler, et al., "Oral Administration of Myelin Induces Antigen-Specific TGF-beta 1 Secreting T Cells in Patients with Multiple Sclerosis," *N.Y. Acad. Sci.*, 835:120-131 (1997), each of which is hereby incorporated by reference in its entirety). Mucosal oral tolerance can be induced by three different mechanisms: active suppression, clonal anergy, and clonal deletion. Antigen dose is the primary factor determining the form of peripheral tolerance that develops. The generation of tolerance due to regulatory T cells (active suppression) is favored by administration of low doses of antigen, whereas administration of high doses of antigen biases toward development of tolerance due to anergy or deletion.

The oral delivery of tissue specific antigens (tolerogens) has generally been accomplished with large or intact proteins which are broken down to fragments by the normal digestive processes (Rosen, et al., "Autoantigens as Substrates for Apoptotic Proteases: Implications for the Pathogenesis of Systemic Autoimmune Disease," *Cell. Death Differ.* 6(1):6-11 (1999); Kweon, et al., "New Insights into Mechanism of Inflammatory and Allergic Diseases in Mucosal Tissues," *Digestion* 63 *Suppl.* S1:1-11 (2001); and Lipkowski, et al., "Protein Hydrolysates for Oral Tolerance," *Biofactors* 12(1-4): 147-150 (2000), each of which is hereby incorporated by reference in its entirety). Specific fragments or peptides are taken up by antigen-presenting cells (M cells) and processed for presentation to undifferentiated T cells. These regulatory T cells release cytokines which suppress inflammation (Marth, et al., "Mechanisms and Applications of Oral Tolerance," *Z. Gastroenterol.* 37(2): 165-185 (1999); Hafler, et al., "Oral Administration of Myelin Induces Antigen-Specific TGF-beta 1 Secreting T Cells in Patients with Multiple Sclerosis," *Ann. N.Y. Acad.*

*Sci.* 835:120-131 (1997), each of which is hereby incorporated by reference in its entirety).

An alternate strategy which is contemplated involves the oral delivery of peptide mimics representative of self tissue antigens displayed on the surface of polymerized nanoparticles along with an M cell targeting molecule, as described in Example 5. Similarly, DNA encoding such antigen with an M cell targeting molecule could be displayed on a nanoparticle vaccine. The processing of tolerogenic peptides or DNA encoding for such peptides (with the appropriate regulatory T cell epitope or none at all) by M cells, the synthesis of tolerogenic peptides in situ and the subsequent presentation to regulatory T cells in the Peyer's patch would lead to mucosal as well as systemic tolerance.

The various self-antigens or tolerogenic peptides that may be presented by way of an M cell directed vaccine as described above include Type II collagen (arthritis) (Weiner, et al., "Oral Tolerance and the Treatment of Rheumatoid Arthritis," *Springer Semin. Immunopathol.* 20(1-2):289-308 (1998), which is hereby incorporated by reference in its entirety), myelin protein MBP, PLP, MOG 9 (multiple sclerosis) (Hafler, et al., "Oral Administration of Myelin Induces Antigen-Specific TGF-beta 1 Secreting T Cells in Patients with Multiple Sclerosis," *Ann. N.Y. Acad. Sci.* 835:120-131 (1997), which is hereby incorporated by reference in its entirety), S—Ag, IRBP (uveitis), ArchR (Myasthenia gravis) (Sempowski, et al., "Effect of Thymectomy on Human Peripheral Blood T Cell Pools in Myasthenia Gravis," *J. Immunol.* 166:2808-2817 (2001), which is hereby incorporated by reference in its entirety), insulin, GAD (type 1 diabetes) (Bach, "Insulin-Dependent Diabetes Mellitus as an Autoimmune Disease," *Endocr. Rev.* 5(4): 516-523 (1994), which is hereby incorporated by reference in its entirety), thyroglobulin (thyroiditis), basement membrane antigen (glomerulonephritis) (Wilson, et al., *In The Kidney*, Brenner and Rector, eds. W. Saunders, Philadelphia (1991), which is hereby incorporated by reference in its entirety) or colonic proteins (colitis). Such antigen materials may be obtained by PCR with human tissue or, by decoding the displayed peptides from phage display using autoimmune antibody directed against the tissue proteins.

Example 11

Tumor Vaccines: Increasing Immunogenicity with the Use of Immunomodulatory Cytokines.

The dominant thrust of current research in tumor immunobiology has focused on defining antigens recognized by human T cells and on augmenting the cellular immune response to tumors. Consequently, the focus of these efforts has been on protein or oligopeptide tumor antigens. Recent studies have focused on the use of vaccines containing oligopeptides or peptides representative of key regions in the tumor cell epitope (Zhou, et al., "An Agonist Anti-Human CD40 Monoclonal Antibody that Induces Dendritic Cell Formation and Maturation and Inhibits Proliferation of a Myeloma Cell Line," *Hybridoma* 18(6):471-478 (1999); Kieber-Emmons, et al., "Cutting Edge: DNA Immunization with Minigenes of Carbohydrate Mimotopes Induce Functional Anti-Carbohydrate Antibody Response," *J. Immunol.* 165(2): 623-627 (2000); which are hereby incorporated by reference in their entirety).

Additionally, it has been shown that cytokines may be used as immunomodulatory adjuvants to be administered in formulations with the tumor vaccines and other vaccines described herein. For instance, liposomes incorporating interferon gamma have been shown to increase the residence time of the cytokine at the vaccination site as compared to cytokine gene transfection of tumor cells (van Slooten et al., "Liposomes Containing Interferon-Gamma as Adjuvant in Tumor Cell Vaccines," *Pharm. Res.* 17(1): 42-8 (2000), which is hereby incorporated by reference in its entirety). It is anticipated by this invention that such liposome nanoparticle vaccines could also be polymerized, which would result in further increased stability of a nanoparticle carrier and allow for an even more prolonged presence of such cytokines, improving the immune response.

Nanoparticle vaccines are contemplated which would elicit an immune response against a given cancer or tumor condition by encapsulation of a cytokine, such as interferon gamma, in a polymerized nanoparticle by the method described in Example 5. Another alternate strategy which is contemplated involves encapsulation of cytokine within a polymerized liposome nanoparticle, along with surface display of tumor specific antigens. The arrangement of such surface displayed tumor antigens could easily be optimized for the immune response desired, using techniques commonly known in the art.

Exemplary tumor specific antigens may be derived from cancers including: leukemia-lymphocytic, granulocytic, monocytic or myelocytic; Lymphomas; basal cell carcinoma; squamous cell carcinoma; breast, colon, endometrial, pancrecatic, lung, etc. carcinoma, and uterine, vaginal, prostatic, testis, ostogenic or pulmonary sarcoma (see Wang, "Human Tumor Antigens: Implications for Cancer Vaccine Development," *J. Mol. Med.* 77(9):640-655 (1999), which is hereby incorporated by reference in its entirety). Tumor antigens according to the invention include 707-AP (707 alanine proline), AFP (alpha ($\alpha$)-fetoprotein), ART-4 (adenocarcinoma antigen recognized by T cells 4), BAGE (B antigen), $\beta$-catenin/m ($\beta$-catenin/mutated), Bcr-abl (breakpoint cluster region-Abelson), CAMEL (CTL-recognized antigen on melanoma), CAP-1 (carcinoembryonic antigen peptide-1), CASP-8 (caspase-8), CDC27m (cell division-cycle 27 mutated), CDK4/m (cycline-dependent kinase 4 mutated) CEA (carcinoembryonic antigen), CT (cancer/testis antigen), Cyp-B (cyclophilin B), DAM ((differentiation antigen melanoma) (the epitopes of DAM-6 and DAM-10 are equivalent, but the gene sequences are different; DAM-6 is also called MAGE-B2 and DAM-10 is also called MAGE-B1), ELF2M (elongation factor 2 mutated), ETV6-AML1 (Ets variant gene 6/acute myeloid leukemia 1 gene ETS), G250 (glycoprotein 250), GAGE (G antigen), GnT-V(N-acetylglucosaminyltransferase V), Gp100 (glycoprotein 100 kD), HAGE (helicose antigen), HER 2/neu (human epidermal receptor-2/neurological), HLA-A*0201-R170I (arginine (R) to isoleucine (I) exchange at residue 170 of the $\alpha$-helix of the $\alpha$-domain in the HLA-A2 gene), HPV-E7 (human papilloma virus E7), HSP70-2M (heat shock protein 70-2 mutated), HST-2 (human signet ring tumor-2), hTERT or hTRT (human telomerase reverse transcriptase), iCE (intestinal carboxyl esterase KIAA0205 (name of the gene as it appears in databases), LAGE (L antigen), LDLR/FUT (low density lipid receptor/GDP-L-fucose: $\beta$-D-galactosidase 2-$\alpha$-L-fucosyltransferase), MAGE (melanoma antigen), MART-1/Melan-A (melanoma antigen recognized by T cells-1/Melanoma antigen A), MC1R (melanocortin 1 receptor), Myosin/m (myosin mutated), MUC1 (mucin 1), MUM-1, -2, -3 (melanoma ubiquitous mutated 1, 2, 3), NA88-A (NA cDNA clone of patient M88), NY-ESO-1=New York-esophageous 1), P15 (protein 15), p190 minor bcr-abl (protein of 190 KD bcr-abl), Pml/RAR$\alpha$ (promyelocytic leukaemia/retinoic acid receptor $\alpha$), PRAME (preferentially expressed antigen of melanoma), PSA (prostate-specific antigen), PSM (prostate-specific membrane antigen), RAGE (renal antigen), RU1 or RU2 (renal ubiquitous 1 or 2), SAGE (sarcoma antigen), SART-1 or SART-3 (squamous antigen rejecting tumor 1 or 3), TEL/AML1 (translocation Ets-family leukemia/acute myeloid leukemia 1), TPI/m (triosephosphate isomerase mutated), TRP-1 (tyrosinase related protein 1, or gp75), TRP-2 (tyrosinase related protein 2), TRP-2/INT2 (TRP-2/intron 2), WT1 (Wilms' tumor gene). These antigens are disclosed in references that are cited in Renkvist, et al., "A Listing of Human Tumor Antigens Recognized by T Cells," *Cancer Immunology Immunotherapy* 50:3-15 (2001), which is hereby incorporated by reference in its entirety. The cited references may be consulted for methods of isolating the specific antigens or genes encoding the specific antigens for use in the vaccines of the invention.

Such nanoparticle vaccine formulations would contain an appropriate amount of cytokine and/or tumor antigen that is optimized to produce the desired response against a given cancerous condition.

The foregoing detailed description has been given for clearness of understanding only and no unnecessary limitations should be understood there from as modifications will be obvious to those skilled in the art. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. A conjugated system comprising:
   polymerized liposomes produced from lipid monomers which do not contain phosphate groups and which are cross-linkable and
   an antigen conjugated to the polymerized liposomes so that the antigen is surface exposed on the polymerized liposomes, wherein the antigen elicits an immune response.

2. The conjugated system according to claim 1, wherein the lipid monomers are selected from the group consisting of fatty acids containing 8-30 carbon atoms in a saturated, monosaturated, or multiply unsaturated form; acylated derivatives of polyamino, polyhydroxy, or mixed aminohydroxy compounds; glycosylacylglycerols; sphingolipids; steroids; terpenes; prostaglandins; non-saponified lipids; and mixtures thereof.

3. The conjugated system according to claim 1, wherein the lipid monomers are diacetylene containing compounds.

4. The conjugated system according to claim 1, wherein the antigen is derived from pathogenic bacterial, fungal or viral organisms, *Streptococcus* species, *Candida* species, *Brucella* species, *Salmonella* species, *Shigella* species, *Pseudomonas* species, *Bordetella* species, *Clostridium* species, Norwalk virus, *Bacillus anthracis, Mycobacterium tuberculosis*, human immunodeficiency virus (HIV),

*Chlamydia* species, human Papillomaviruses, Influenza virus, Paramyxovirus species, Herpes virus, Cytomegalovirus, Varicella-Zoster virus, Epstein-Barr virus, Hepatitis viruses, *Plasmodium* species, *Trichomonas* species, sexually transmitted disease agents, viral encephalitis agents, protozoan disease agents, fungal disease agents, bacterial disease agents, cancer cells, or mixtures thereof.

5. The conjugated system according to claim 1, wherein the conjugated system further comprises:
   a targeting agent associated with the conjugated system to direct the antigen to a particular in vivo location.

6. The conjugated system according to claim 5, wherein the targeting agent directs the antigen to a mucosal membrane.

7. The conjugated system according to claim 1, wherein the conjugated system comprises a combination of different antigens.

8. The conjugated system according to claim 1, wherein the antigen is chemically complexed to an outer surface of the polymerized liposomes.

9. The conjugated system according to claim 8, wherein the antigen is ionically bound to an outer surface of the polymerized liposomes.

10. The conjugated system according to claim 8, wherein the antigen is non-ionically bound to an outer surface of the polymerized liposomes.

11. The conjugated system according to claim 1, wherein the antigen is covalently bound to an outer surface of the polymerized liposomes.

12. The conjugated system according to claim 1, wherein the antigen is attached to reactive head groups of the lipid monomers.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:  Synthetic

<400> SEQUENCE: 1

Tyr Arg Gln Phe Val Thr Gly Phe Trp
 1               5

<210> SEQ ID NO 2
<211> LENGTH: 9
<212> TYPE: PRT
<213> ORGANISM: J404phage

<400> SEQUENCE: 2

Trp Glu Asn Trp Met Met Gly Asn Ala
 1               5

<210> SEQ ID NO 3
<211> LENGTH: 12
<212> TYPE: PRT
<213> ORGANISM: J404phage

<400> SEQUENCE: 3

Phe Asp Thr Gly Ala Phe Asp Pro Asp Trp Pro Ala
 1               5                  10
```